United States Patent [19]

Brunner

[11] Patent Number: 4,872,902

[45] Date of Patent: Oct. 10, 1989

[54] CYCLOHEXANEDIONES AND THEIR USE AS PLANT GROWTH REGULATORS

[75] Inventor: Hans-Georg Brunner, Lausen, Switzerland

[73] Assignee: Ciba-Geigy Corporation, Ardsley, N.Y.

[21] Appl. No.: 153,376

[22] Filed: Feb. 8, 1988

[30] Foreign Application Priority Data

Feb. 9, 1987 [CH] Switzerland .......................... 469/87

[51] Int. Cl.[4] ...................... A01N 33/02; A01N 33/08; C07C 149/40; C07C 101/44

[52] U.S. Cl. .......................................... 71/105; 560/9; 560/11; 560/12; 560/13; 560/17; 560/18; 560/19; 560/20; 560/21; 560/22; 560/23; 560/43; 560/45; 560/126; 564/47; 564/48; 564/49; 564/50; 564/52; 564/53; 564/54; 564/56; 564/57; 564/189; 564/190; 564/192; 564/201; 564/210; 564/214; 564/215; 564/217; 564/218; 564/221; 564/223; 71/92; 71/94; 71/95; 71/106; 71/107; 71/111; 71/118; 71/119; 71/120; 544/163; 544/169; 546/226; 548/538; 558/415; 558/416

[58] Field of Search .................... 558/415, 416; 560/9, 560/11, 12, 13, 17, 18, 19, 20, 21, 22, 23, 43, 45, 126; 564/47, 48, 49, 50, 52, 53, 54, 56, 57, 189, 190, 192, 201, 210, 214, 215, 217, 218, 221, 223; 71/105, 106, 107, 111, 118, 119, 120

[56] References Cited

U.S. PATENT DOCUMENTS

| | | | |
|---|---|---|---|
| 4,002,767 | 1/1977 | Aldrich et al. | 424/322 |
| 4,487,783 | 12/1984 | Grohe et al. | 424/322 |
| 4,584,013 | 4/1986 | Brunner | 71/94 |
| 4,618,360 | 10/1986 | Brunner | 71/88 |
| 4,623,382 | 11/1986 | Brunner | 71/94 |
| 4,640,706 | 2/1987 | Brunner | 71/94 |
| 4,693,745 | 9/1987 | Brunner | 71/94 |

*Primary Examiner*—Mary C. Lee
*Assistant Examiner*—J. Richter
*Attorney, Agent, or Firm*—Kevin T. Mansfield; Edward McC. Roberts

[57] ABSTRACT

The invention relates to the novel cyclohexanediones of formula I

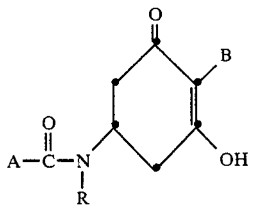

(I)

in which
R is hydrogen or $C_1$–$C_6$-alkyl,
A is $R_2$, $OR_3$ or $NR_3R_4$,
$R_2$ is $C_1$–$C_6$-alkyl that is unsubstituted or is mono-substituted by $C_1$–$C_4$-alkoxy or mono- or poly-substituted by halogen, or is $C_3$–$C_6$-cycloalkyl,
$R_3$ is $C_1$–$C_6$-alkyl or $C_3$–$C_6$-cycloalkyl, or is phenyl or benzyl each of which is unsubstituted or is mono-, di- or tri-substituted by $R_5$,
$R_4$ is hydrogen, $C_1$–$C_6$-alkyl, $C_1$–$C_4$-alkoxy or $C_3$–$C_6$-cycloalkyl,
$R_3$ and $R_4$ are, in addition, together with the nitrogen atom to which they are bonded, a pyrrolidine, morpholine or piperidine radical,
B is one of the radicals

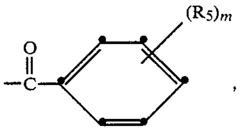

, 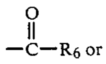 or 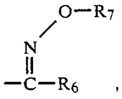 , m is 0, 1, 2 or 3,
$R_5$ is halogen, nitro, cyano, $C_1$–$C_4$-alkyl, $C_1$–$C_4$-alkoxy, $C_1$–$C_4$-alkylthio, $C_1$–$C_4$-haloalkyl, $C_1$–$C_4$-alkylsulphinyl or $C_1$–$C_4$-alkylsulphonyl,
$R_6$ is $C_1$–$C_6$-alkyl or $C_3$–$C_6$-cycloalkyl, and
$R_7$ is hydrogen, $C_1$–$C_6$-alkyl, $C_1$–$C_6$-haloalkyl, $C_3$–$C_6$-alkenyl, $C_3$–$C_6$-haloalkenyl or $C_3$–$C_6$-alkynyl, and to salts of the compounds of formula I with acids, bases or complex-formers, to processes for the preparation thereof and to novel intermediates. The compounds of formula I have herbicidal and growth-regulating action.

14 Claims, No Drawings

CYCLOHEXANEDIONES AND THEIR USE AS PLANT GROWTH REGULATORS

NOVEL CYCLOHEXANEDIONES

The present invention relates to novel cyclohexanediones having herbicidal and growth-regulating action, to agrochemical compositions containing those cyclohexanediones, to their use for controlling undesired plant growth and for regulating plant growth and to processes for the preparation of the compounds according to the invention. The invention also relates to novel intermediates and to processes for the preparation thereof.

Numerous 2,5-di-substituted cyclohexane-1,3-diones having herbicidal action have already become known. These compounds are not always satisfactory with regard to strength of action, duration of action, selectivity and range of application. In contrast, it has surprisingly been found that the novel 2,5-di-substituted cyclohexane-1,3-diones of the general formula I have good herbicidal and growth-regulating action.

The invention relates to the novel cyclohexane-1,3-diones of formula I

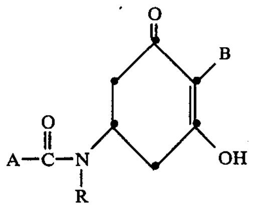

(I)

in which

R is hydrogen or $C_1$–$C_6$-alkyl,

A is $R_2$, $OR_3$ or $NR_3R_4$, $R_2$ is $C_1$–$C_6$-alkyl that is unsubstituted or is mono-substituted by $C_1$–$C_4$-alkoxy or mono- or poly-substituted by halogen, or is $C_3$–$C_6$-cycloalkyl, $R_3$ is $C_1$–$C_6$-alkyl or $C_3$–$C_6$-cycloalkyl, or is phenyl or benzyl each of which is unsubstituted or is mono-, di- or tri-substituted by $R_5$, $R_4$ is hydrogen, $C_1$–$C_6$-alkyl, $C_1$–$C_4$-alkoxy or $C_3$–$C_6$-cycloalkyl, $R_3$ and $R_4$ are, in addition, together with the nitrogen atom to which they are bonded, a pyrrolidine, morpholine or piperidine radical, B is one of the radicals

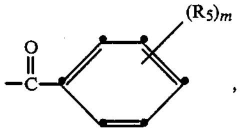 , 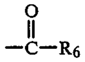 or 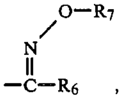 , m is 0, 1, 2 or 3, $R_5$ is halogen, nitro, cyano, $C_1$–$C_4$-alkyl, $C_1$–$C_4$-alkoxy, $C_1$–$C_4$-alkylthio, $C_1$–$C_4$-haloalkyl, $C_1$–$C_4$-alkylsulphinyl or $C_1$–$C_4$-alkylsulphonyl, $R_6$ is $C_1$–$C_6$-alkyl or $C_3$–$C_6$-cycloalkyl, and $R_7$ is hydrogen, $C_1$–$C_6$-alkyl, $C_1$–$C_6$-haloalkyl, $C_3$–$C_6$-alkenyl, $C_3$–$C_6$-haloalkenyl or $C_3$–$C_6$-alkynyl, and to salts of the compounds of formula I with acids, bases or complexformers.

Within the scope of the invention disclosed herein, the generic terms cover, for example, the individual substituents mentioned hereinafter, although this list does not constitute a limitation of the invention.

Alkyl includes the straight-chain or branched $C_1$–$C_6$-alkyls such as methyl, ethyl, n-propyl, isopropyl, n-butyl, isobutyl, tert.-butyl and the isomers of pentyl and hexyl.

Halogen is fluorine, chlorine, bromine and iodine; especially fluorine and chlorine.

$C_1$–$C_4$-alkoxy is methoxy, ethoxy, n-propoxy, isopropoxy and the isomers of butoxy. Methoxy and ethoxy are preferred.

$C_1$–$C_4$-alkoxy-$C_1$–$C_4$-alkyl includes the isomers of alkoxyalkyl that can be derived from the alkoxy and alkyl radicals within the scope of the above definition. $C_1$–$C_2$-alkoxy-$C_1$–$C_2$-alkyl, such as methoxymethyl, ethoxymethyl, 2-methoxyethyl, 1-methoxyethyl or 2-ethoxyethyl, is preferred.

Haloalkyl should be understood as meaning the alkyl radicals that are completely or partially substituted by identical or different halogen atoms, in accordance with the scope of the definition in each case; for example trifluoromethyl, trichloromethyl, chloromethyl, dichloromethyl, 2,2,2-trifluoroethyl, etc.

The $C_3$–$C_6$-alkenyl, $C_3$–$C_6$-haloalkenyl and $C_3$–$C_6$-alkynyl radicals are bonded by way of a saturated carbon atom to the oxygen atom of the oxime group. The allyl and propargyl radicals and the 3-chloroprop-2-en-1-yl radical are preferred.

$C_3$–$C_6$-cycloalkyl is cyclopropyl, cyclobutyl, cyclopentyl and cyclohexyl. Special mention should be made of cyclopropyl and cyclohexyl.

In cases where a substituent, for example $R_5$, may occur a number of times, its meanings can be freely selected from the group of radicals assigned to that substituent.

While observing the scope of definition of the other substituents, the compounds of formula I can, with regard to their structure, be referred to as (a) cyclohexyl-phenyl-ketones (where

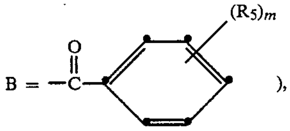

), (b) cyclohexyl-alkyl-ketones (where

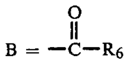

and $R_6$+$C_1$–$C_6$-Alkyl), (c) cyclohexyl-cycloalkyl-ketones (where

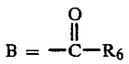

and $R_6$=$C_3$–$C_6$-cycloalkyl), (d) oximes (where

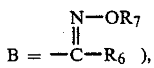

), (e) ureas (where $A=NR_3R_4$), (f) urethanes (where $A=OR_3$) or (g) carbamides (where $A=R_2$).

Special mention should be made of compounds of formula I,

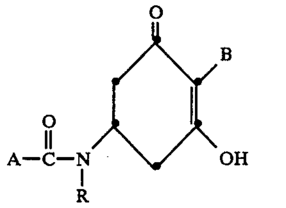

(I)

in which

R is hydrogen or $C_1$–$C_4$-alkyl,

A is $R_2$, $OR_3$ or $NR_3R_4$, $R_2$ is cyclopropyl, cyclopentyl or cyclohexyl, or is $C_1$–$C_4$-alkyl that is unsubstituted or is mono-substituted by $C_1$–$C_4$-alkoxy or mono- or poly-substituted by halogen, $R_3$ is $C_1$–$C_4$-alkyl, cyclopropyl, cyclopentyl or cyclohexyl, or is phenyl or benzyl each of which is unsub- stituted or is mono- or di-substituted by $R_5$, $R_4$ is hydrogen, $C_1$–$C_4$-alkyl, methoxy, cyclopropyl, cyclopentyl or cyclohexyl, $R_3$ and $R_4$ are, in addition, together with the nitrogen atom to which they are bonded, a pyrrolidine, morpholine or piperidine radical, B is one of the radicals

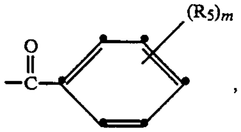 , 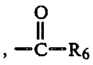 or 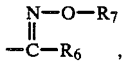 , m is 0, 1, 2 or 3, $R_5$ is fluorine, chlorine, bromine, nitro, cyano, $C_1$–$C_4$-alkyl, $C_1$–$C_4$-alkoxy, $C_1$–$C_4$-alkylthio, trifluoromethyl, $C_1$–$C_4$-alkylsulphinyl or $C_1$–$C_4$-alkylsulphonyl, $R_6$ is $C_1$–$C_4$-alkyl, cyclopropyl, cyclopentyl or cyclohexyl, and $R_7$ is hydrogen, $C_1$–$C_4$-alkyl, $C_1$–$C_4$-haloalkyl, $C_3$–$C_4$-alkenyl, $C_3$–$C_4$-haloalkenyl or $C_3$–$C_4$-alkynyl.

Preferred are the compounds of formula I

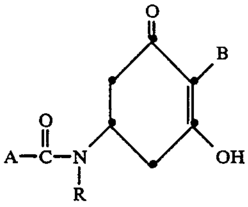

(I)

in which

R is hydrogen or $C_1$–$C_3$-alkyl,

A is $R_2$, $OR_3$ or $NR_3R_4$, $R_2$ is $C_1$–$C_4$-alkyl, methoxymethyl or trifluoromethyl, $R_3$ is $C_1$–$C_4$-alkyl, cyclopropyl, cyclohexyl or benzyl, or is phenyl that is unsubstituted or is substituted by chlorine, methoxy or by methyl, $R_4$ is hydrogen, methyl, methoxy or ethyl, $R_3$ and $R_4$ are, in addition, together with the nitrogen atom to which they are bonded, a pyrrolidine or piperidine radical, B is one of the radicals

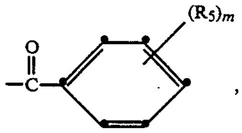 , 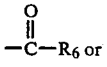 or 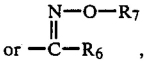 , m is 0, 1, 2 or 3, $R_5$ is fluorine, chlorine, bromine, nitro, methyl, methoxy, trifluoromethyl, $C_1$–$C_4$-alkylthio, $C_1$–$C_4$-alkylsulphinyl or $C_1$–$C_4$-alkylsulphonyl, $R_6$ is $C_1$–$C_6$-alkyl, cyclopropyl or cyclohexyl, and $R_7$ is methyl, ethyl, allyl, propargyl or 3-chloro-prop-2-en-1-yl.

Especially preferred are the compounds of formula I

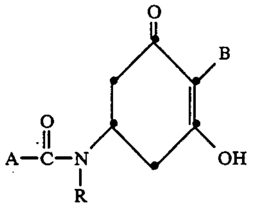

(I)

in which

R is hydrogen or $C_1$–$C_3$-alkyl,

A is $R_2$, $OR_3$ or $NR_3R_4$, $R_2$ is methoxymethyl or $C_1$–$C_4$-alkyl, $R_3$ is $C_1$–$C_4$-alkyl or is phenyl that is unsubstituted or is substituted by chlorine or by methyl, $R_4$ is hydrogen or methyl, $R_3$ and $R_4$ are, in addition, together with the nitrogen atom to which they are bonded, a pyrrolidine radical, B is one of the radicals

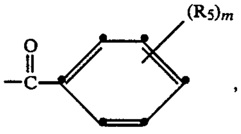 , 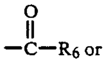 or 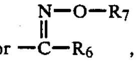 , m is 0, 1 or 2, $R_5$ is chlorine, nitro, trifluoromethyl, methylthio, methylsulphinyl or methylsulphonyl, $R_6$ is $C_1$–$C_3$-alkyl or cyclopropyl, and $R_7$ is methyl, allyl, ethyl or 3-chloro-prop-2-em-1-yl.

In view of their herbicidal, resp. plant growth regulatory activity the following compounds have to be mentioned individually 2-Butanoyl-5-ethoxycarbonylaminocyclohexan-1,3-dione, 2-Propanoyl-5-(N',N'-dimethylureido)-cyclohexan-1,3-dione, 2-Butanoyl-5-(N',N'-dimethylureido)-cyclohexan-1,3-dione, 5-Acetamido-2-propanoyl-cyclohexan-1,3-dione,
2-(2,4-Dichlorbenzoyl)-5-ethoxycarbonylamino-cyclohexan-1,3-dione,
2-(2,4-Dichlorbenzoyl)-5-(N'-isopropylureido)-cyclohexan-1,3-dione,
2-(2,4-Dichlorbenzoyl)-5-(N',N'-dimethylureido)-cyclohexan-1,3-dione,
5-(N'-tert-Butylureido)-2-(1-allyloxyiminobutyl)-cyclohexan-1,3-dione,
5-(N',N'-Dimethylureido)-2-(1-ethoxyiminopropyl)-cyclohexan-1,3-dione,
5-(N'-Phenylureido)-2-(1-ethoxyiminobutyl)-cyclohexan-1,3-dione,
5-(N'-Phenylureido)-2-[1-(3-chlorallyl)oxyiminobutyl]-cyclohexan-1,3-dione,
5-(N'-Phenylureido)-2-(1-ethoxyiminoethyl)-cyclohexan-1,3-dione,
5-(N'-Phenylureido)-2-(1-methoxyiminobutyl)-cyclohexan-1,3-dione,
5-[N'-(2-Methylphenyl)-ureido]-2-(1-ethoxyiminobutyl)-cyclohexan-1,3-dione and
5-[N'-(3-Chlorphenyl)-ureido]-2-(1-ethoxyiminobutyl)-cyclohexan-1,3-dione.

The cyclohexanediones of formula I are in tautomeric equilibrium in accordance with the following equation:

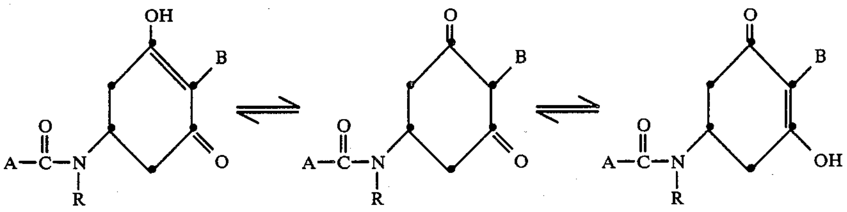

(I) (I') (I)

The diketones of formula I, which are readily enolisable in accordance with the equilibrium system I⇌I'⇌I, form salts even with relatively weak bases. In the salts resulting therefrom, the compounds of formula I form the anionic moiety. Suitable cations are: alkaline earth metal, alkali metal and ammonium ions. Apart from the unsubstituted ammonium ion, ammonium ions should be understood as being the various mono-, di-, tri-and tetra-alkylammonium ions. The formation of suitable salts can influence, inter alia, the water-solubility and, overall, the bio-availability and the spectrum of action of the compounds of formula I.

The compounds of formula I can be prepared in the following manner:

(a) a cyclohexanedione of formula II is reacted with a compound of

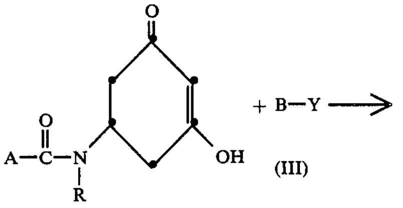

(III)

(II)

-continued

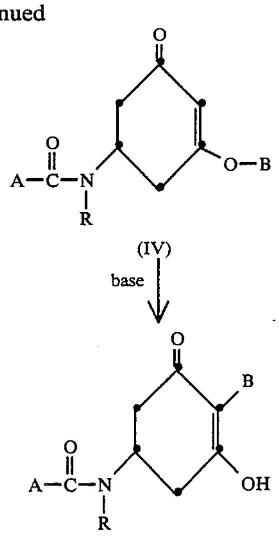

(IV)

(I)

formula III to form a compound of formula IV which is then thermally rearranged in the presence of a base to form a compound of formula I, with A, B and R being as defined hereinbefore but with the limitation that B is not the oxime ether group

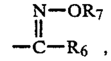
, and Y being a nucleofugal group, such as chlorine, bromine or $C_1$-$C_4$-alkoxy, that can be removed under the reaction conditions, or (b) a cyclohexanedione of formula II is reacted with a compound

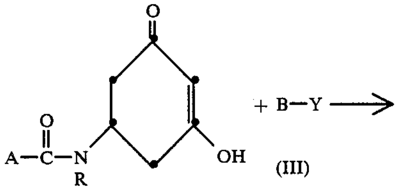

(III)

(II)

-continued

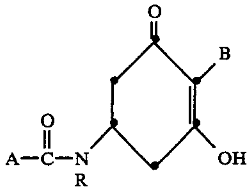

(I)

of formula III in which Y is a cyano group, in the presence of a base and $ZnCl_2$, to form a compound of formula I, the radicals A, R and B in formulae I, II and III being as defined hereinbefore, with the proviso that B is not the oxime ether group

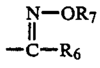

or (c) a cyclohexyl ketone of formula Ia is reacted with a

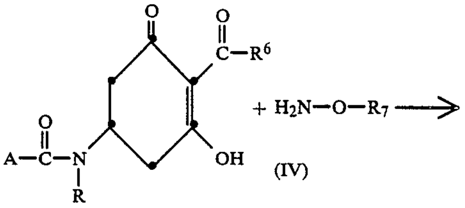

(Ia)

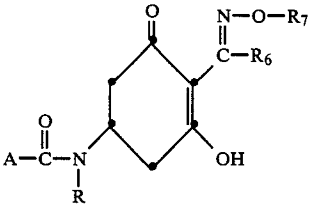

(Ib)

hydroxylamine of formula IV to form an oxime of formula Ib.

The cyclohexanones of formulae II and IV which are used as intermediates are also novel. They are valuable educts for the preparation of compounds of formula I.

The invention thus also relates to the novel cyclohexanones of formula II (II)

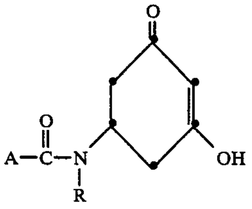

in which A and R are as defined under formula I, and to the novel cyclohexanones of formula IV (IV)

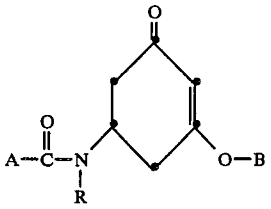

in which A and R and B are as defined under formula I, with the proviso that B is not the oxime ether group

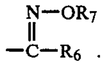

The compounds of formula II can be prepared in the following manner:

(a) a resorcinol of formula V is hydrogenated in accordance with methods known per se

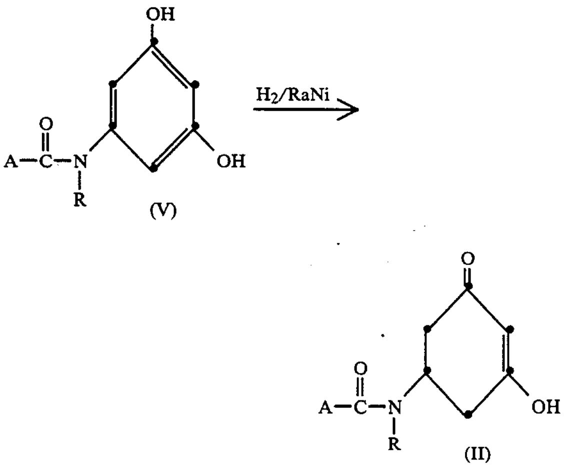

the substituents A and R being as defined hereinbefore, or (b) an isocyanate of formula VI is reacted with an alcohol or an amine of formula VII or VIII, respectively,

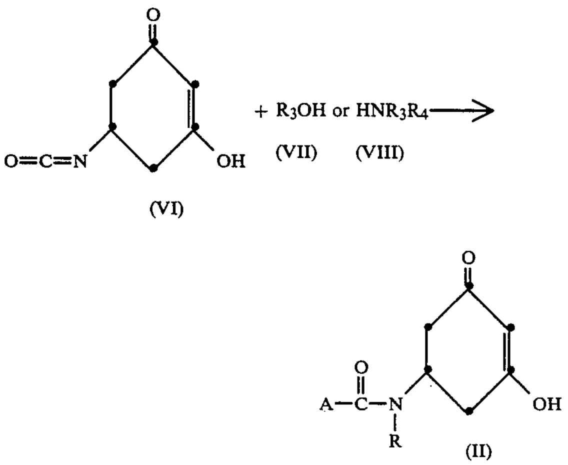

to form a urethane or urea of formula II in which R is hydrogen and A is $OR_3$ or $NR_3R_4$ and $R_3$ and $R_4$ are as defined hereinbefore.

The resorcinols of formula V required as starting compounds can be prepared analogously to known processes [J. Org. Chem. 40 (1975), 1556; Helv. Chim. Acta 56 (1973) 510]by reacting phloroglucinol IX with amines of formula X to form the aminoresorcinols of formula XI. Starting from the aminoresorcinols XI, the N-acylated

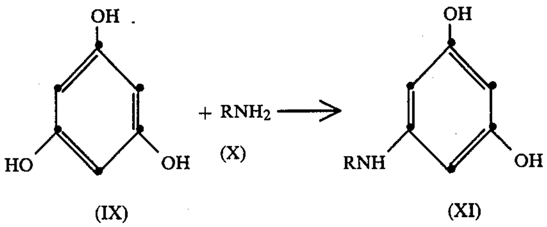

(IX) (XI)

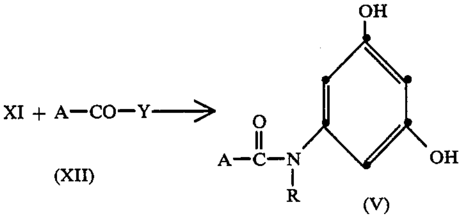

(XII) (V)

compounds of formula V are readily obtainable by reaction with XII. The radicals R and A in the above reaction scheme correspond to the definition of formula I, and Y is a nucleofugal group, such as halogen, $C_1$-$C_4$-alkoxy or phenoxy, that can be removed under the reaction conditions.

The urethanes and ureas of formula II in which A is $OR_3$ or $NR_3R_4$ can be prepared by an alternative method of synthesis starting from the cyclohexanecarboxylic acid XIII.

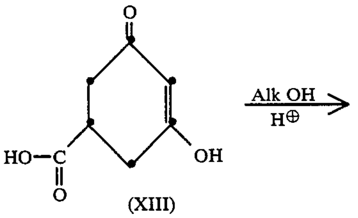

(XIII)

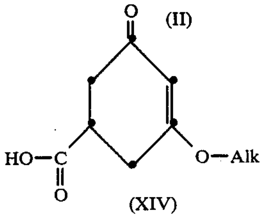

(XIV)

For that purpose, the monoether XIV, in which Alk=$C_1$-$C_4$-alkyl, is first of all prepared from XIII and it is then converted according to Curtius via azide into the isocyanate XV.

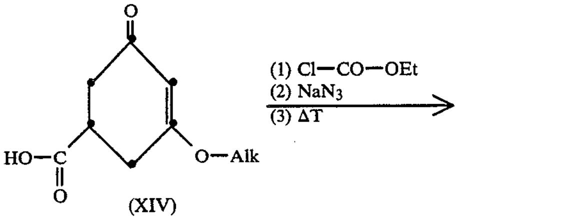

(XIV)

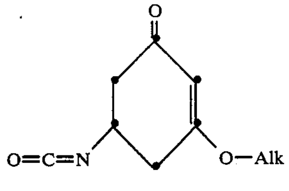

(XV)

XV + ROH oder $HNR_3R_4$ (VII) (VIII)

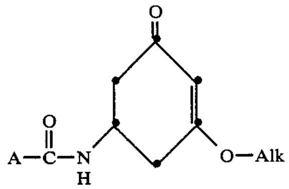

(XVI)

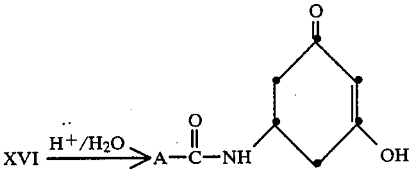

II

Compound XVI is then readily obtainable from XV by adding the alcohols VII or the amines VIII. The desired end product II can be generated from XVI by cleaving ether.

The novel compounds of formula II are in tautomeric equilibrium II⇄II'⇄II with the diketo form II'

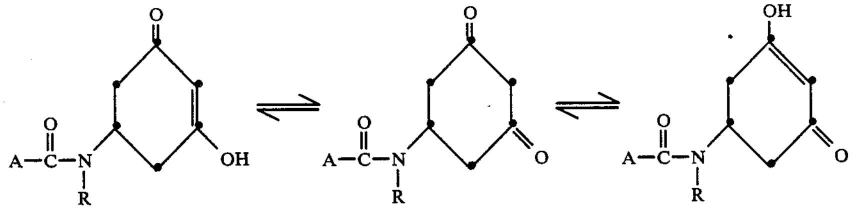

(II) (II') (II)

The compounds of formula I are highly active plant growth regulating ingredients which, at suitable rates of application, are eminently suitable as selective herbicides for controlling weeds in crops of useful plants. That is to say, at those rates of application, the compounds of formula I are distinguished by good selective-herbicidal properties against weeds. Cultivated plants such as rye, barley, oats, wheat, maize, sorghum, rice, cotton and soya are practically undamaged when low rates of application are used. The growth of the cultivated plants is influenced only negligibly in the case of increased rates of application. If very high rates of application are used, the compounds of formula I exhibit total-herbicidal properties.

The selective herbicidal action of the compounds according to the invention is observed both in preemergence and postemergence use. These compounds can therefore be used very successfully in the preemergence process and in the postemergence process for the selective control of weeds.

The compounds of formula I have in addition pronounced growth-regulating, especially growth-inhibiting, properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area.

A further mechanism of yield increase using growth regulators resides in the fact that nutrients are able increasingly to promote flower formation and fruiting, whilst vegetative growth is inhibited.

At higher rates of application of compounds of formula I, all tested plants are so severely damaged in their development that they die.

The invention also relates to herbicidal and growth-regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl- sulphoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both so-called water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulphonates, fatty sulphates, sulphonated benzimidazole derivatives or alkylaryl- sulphonates.

The fatty sulphonates or sulphates are usually in the form of alkali metal salts, alkaline earth metal salts or unsubstituted or substituted ammonium salts and contain a $C_8$–$C_{22}$-alkyl radical which also includes the alkyl moiety of acyl radicals, e.g. the sodium or calcium salt of lignosulphonic acid, of dodecylsulphate or of a mixture of fatty alcohol sulphates obtained from natural fatty acids.

These compunds also comprise the salts of sulphuric acid esters and sulphonic acids of fatty alcohol/ethylene oxide adducts. The sulphonated benzimidazole derivatives preferably contain 2 sulphonic acid groups and one fatty acid radical containing 8 to 22 carbon atoms. Examples of alkylarylsulphonates are the sodium, calcium or tri- ethanolamine salts of dodecylbenzensulphonic acid, dibutylnaphthalenesulphonic acid, or of a naphthalene- sulphonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or of saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine polypropylene glycol and alkylpolypropylene glycol containing 1 to 10 carbon atoms in the alkyl chain, which adducts contain 20 to 250 ethylene glycol ether groups and 10 to 100 propylene glycol ether groups. These mentioned compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan such as polyoxyethylene sorbitan trioleate are also suitable non-ionic surfactants.

Cationic surfactants are preferably quaternary ammonium salts which contain, as N-substituent, at least one $C_8$–$C_{22}$-alkyl radical and, as further substituents, lower unsubstituted or halogenated alkyl, benzyl or lower hydroxyalkyl radicals. The salts are preferably in the form of halides, methylsulphates or ethylsulphates, e.g. stearyltrimethylammonium chloride or benzyldi(2-chloro- ethyl)ethylammonium bromide.

The surfactants customarily employed in the art of formulation are described e.g. in the following publications:

1985 International McCutcheon's Emulsifiers and Detergents, Glen Rock, N.J. U.S.A.;

H. Stache, "Tensid-Taschenbuch", 2nd Edition, C. Hanser Verlag, Munich & Vienna, 1981;

M. and J. Ash, "Encyclopedia of Surfactants", Vol. I-III, Chemical Publishing Co., New York, 1980-81.

The compositions usually contain 0.1 to 95%, preferably 0.1 to 80%, of a compound of formula I, 1 to 99.9% of one or more solid or liquid adjuvants, and 0 to 25% of a surfactant.

Preferred formulations are composed in particular of the following constituents (% = percentage by weight):

| | | |
|---|---|---|
| Emulsifiable concentrates | | |
| active ingredient: | 1 to 20%, | preferably 5 to 10% |
| surfactant: | 5 to 30%, preferably 10 to 20% | |
| liquid carrier: | 50 to 94%, | preferably 70 to 85% |
| Dusts | | |
| active ingredient: | 0.1 to 10%, | preferably 0.1 to 1% |
| solid carrier: | 99.9 to 90%, | preferably 99.9 to 99% |
| Suspension concentrates | | |
| active ingredient: | 5 to 75%, | preferably 10 to 50% |
| water: | 94 to 25%, | preferably 88 to 30% |
| surfactant: | 1 to 40%, | preferably 2 to 30% |
| Wettable powders | | |
| active ingredient: | 0.5 to 90%, | preferably 1 to 80% |
| surfactant: | 0.5 to 20%, | preferably 1 to 15% |
| solid carrier: | 5 to 95%, | preferably 15 to 90% |
| Granulates | | |
| active ingredient: | 0.5 to 30%, | preferably 3 to 15% |
| solid carrier: | 99.5 to 70%, | preferably 97 to 85%. |

Whereas commercial products will be preferably formulated as concentrates, the end user will normally employ dilute formulations. The formulations can be diluted to a concentration as low as 0.001%. The rates of application are normally from 0.001 to 4 kg a.i./ha, preferably from 0.005 to 1 kg a.i./ha.

The compositions may also contain further auxiliaries such as stabilisers, antifoams, viscosity regulators, binders, tackifiers as well as fertilisers or other active ingredients for obtaining special effects.

PREPARATION OF THE STARTING COMPOUNDS

H.O.1. 5-aminoresorcinol 500 g (4 moles) of phloroglucinol are introduced in portions into 4 liters of a 30% aqueous ammonia solution, and then $NH_3$ gas is introduced over a period of 40 minutes. After stirring for twenty-four hours at room temperature, the resulting clear brown solution is concentrated at 45° C. under a water-jet vacuum. The solid that remains is triturated with toluene and a small amount of acetone, filtered off with suction and dried at 45° C. in vacuo.

464 g (92.8%) of the title compound of formula

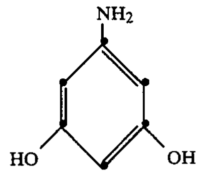

are isolated in the form of crystals having a melting point of 150° C.

H.O.2. 5-(methylamino)-resorcinol 140 ml of a 40% aqueous methylamine solution are added dropwise at 25° C. to a solution of 189 g (1.5 moles) of phloroglucinol in 1500 ml of dimethylformamide and 1000 ml of water. The whole is subsequently stirred for 20 hours at room temperature and then the solvent is distilled off at 70° C. in vacuo and drying is carried out under a high vacuum.

The residue is then triturated with diethyl ether and dried.

173 g (83%) of the title compound of formula

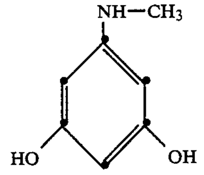

are isolated in the form of crystals having a melting point of 130° C.

H.O.3. 3-methoxy-cyclohex-3-en-5-one-carboxylic acid 10 ml of concentrated sulphuric acid are added to a solution of 1560 g (10 moles) of cyclohexane-3,5-dione-carboxylic acid in 3 liters of methanol and the whole is left at from 20° to 25° C. for 3 hours while stirring. 3 liters of diethyl ether are then added and the precipitated product is filtered off with suction.

1508 g (88.7%) of the title compound of formula

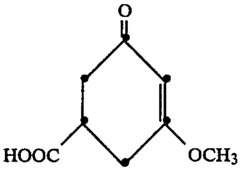

are isolated.

H.1 PREPARATION OF COMPOUNDS OF FORMULA V

H.1.1. N-isopropyl-N'-(3,5-dihydroxyphenyl)-urea 52 ml (0.53 mole) of isopropyl isocyanate are added dropwise over a period of 20 minutes to a solution of 62.5 g (0.5 mole) of 5-aminoresorcinol in 1000 ml of dioxan, the internal temperature rising to 35° C. The whole is subsequently stirred for 5 hours at room temperature and then 1000 ml of petroleum ether are added whereupon the title compound is precipitated in the form of fine crystals.

162 g (84%) of the title compound of formula

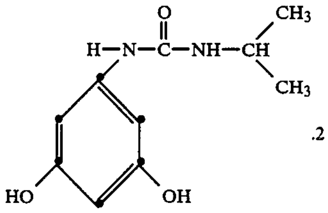

.2 $C_4H_8O_2$ are isolated in the form of crystals having a melting point of >210° C. (decomposition); the crystals of the title compound contain 2 molar equivalents of dioxan. (Compound No. 1.04).

H.1.2. N-isopropyl-N'-methyl-N'-(3,5-dihydroxyphenyl)-urea

Analogously to Example H.1.1., there are obtained from 69.5 g (0.5 mole) of 5-methylaminoresorcinol and 52 ml (0.53 mole) of isopropyl isocyanate 113 g (84%) of the title compound of formula

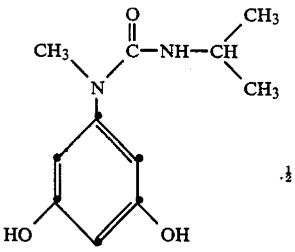

·½ $C_4H_8O_2$ in the form of crystals having a melting point of >230° C. (decomposition); the crystals of the title compound contain 0.5 molar equivalent of dioxan (Compound No. 1.022).

H.1.3. 5-acetamidoresorcinol 10.4 ml (0.11 mole) of acetic anhydride are added dropwise to a solution of 12.5 g (0.1 mole) of 5-aminoresorcinol in 100 ml of dioxan in such a manner that the internal temperature does not exceed 50° C. The whole is subsequently stirred for 2 hours and then 200 ml of petroleum ether are added whereupon the product precipitates.

15.3 g (91.7%) of the title compound of formula

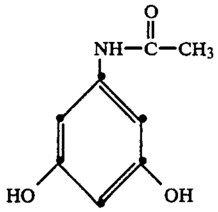

are isolated in the form of crystals having a melting point of >200° C. (decomposition) (Compound No. 1.011).

H.1.4. N-(3,5-dihydroxyphenyl)-carbamic acid phenyl ester 410 ml Phenyl chloroformate are dropped under cooling at 15° to 20° C. to a mixture of 375 g 5-aminoresorcinol, 270 g sodium acetate and 30 ml dimethylformamid in 3 l dioxane. It is then stirred for one hour at 20° to 25° C., diluted with 3 l ethyl acetate and filtered off from the sodium chloride precipitated. After the solvent is destillated off the residue is crystallised from petrol ether.

868 g (87%) of the title compound of formula

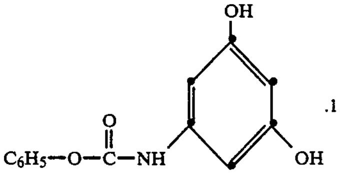

.1 $C_4H_8O_2$ are isolated in the form of crystals having a melting point of 176° C. (decomposition) (Compound No. 1.031).

H.1.5. N,N-dimethyl-N'-(3,5-dihydroxyphenyl)-urea

To a solution of 840 g N-(3,5-dihydroxyphenyl)-carbamic acid phenylester in 2,5 l ethanol 900 ml of a 33% solution of dimethylamine in ethanol are added. After stirring for 10 hours at 20° to 25° C. the solvent is distilled off in vacuo.

The slurry thus obtained is digerated with diethylether for several times and then filtrated by sucction.

469 g (95%) of the title compound of formula

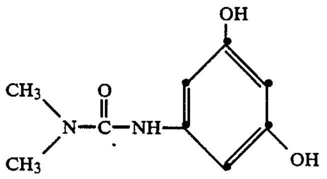

are isolated in the form of crystals having a melting point of 230° C. (Compound No. 1.014).

The compounds in Table 1 can be prepared in an analogous manner.

TABLE 1

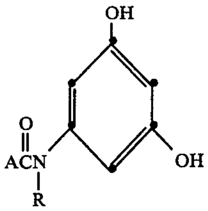

| No. | R | A | phys. constant |
|---|---|---|---|
| 1.001 | H | $NHCH_3$ | m.p. 215° C. (.1 dioxan) |
| 1.002 | H | $NHC_2H_5$ | m.p. 98–100° C. (.1¼ dioxan) |
| 1.003 | H | $NHC_3H_7$ | |
| 1.004 | H | $NHC_3H_7$ (i) | m.p. >210° C. (decomp.) (.2 dioxan) |
| 1.005 | H | $NHC_4H_9$ (n) | |
| 1.006 | H | $NHC_4H_9$ (t) | m.p. 115–118° (.1 dioxan) |
| 1.007 | H | $OCH_3$ | |
| 1.008 | H | $OC_2H_5$ | m.p. 152–153° |
| 1.009 | H | $OC_3H_7$ | |
| 1.010 | H | $OC_3H_7$ (i) | |
| 1.011 | H | $CH_3$ | m.p. >200° decomp. |
| 1.012 | H | $C_2H_5$ | m.p. >190° decomp. |
| 1.013 | H | $C_4H_9$ | |
| 1.014 | H | $N(CH_3)_2$ | m.p. >230° C. |
| 1.015 | H | $N(C_2H_5)_2$ | |
| 1.016 | H | 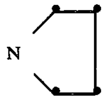 | m.p. >230° C. |
| 1.017 | H | 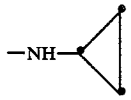 | |
| 1.018 | H | 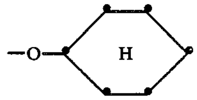 | |
| 1.019 | H | 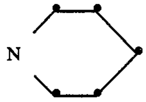 | |
| 1.020 | $-CH_3$ | $NHCH_3$ | m.p. >170° C. |
| 1.021 | $-CH_3$ | 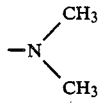 | |
| 1.022 | $-CH_3$ | $-NH-C_3H_7$ (i) | m.p. >230° C. (.½ dioxan) |
| 1.023 | $-CH_3$ | $-OCH_3$ | |
| 1.024 | $-CH_3$ | $-OC_3H_7$ (i) | |
| 1.025 | $-CH_3$ | $-CH_3$ | m.p. >185° C. (decomp.) |
| 1.026 | $-CH_3$ | $-C_2H_5$ | m.p. >100° C. (decomp.) (.¼ dioxan) |
| 1.027 | $-C_2H_5$ | $-NHCH_3$ | |
| 1.028 | $-C_2H_5$ | $-N(CH_3)_2$ | |
| 1.029 | $-C_3H_7$ (i) | $-NHCH_3$ | |
| 1.030 | $-CH_3$ | 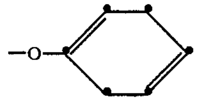 | m.p. 140–143° (.0,5 dioxan) |
| 1.031 | $-H$ | 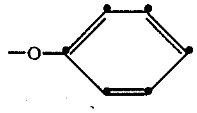 | m.p. 175–176° (.½ dioxan) |

TABLE 1-continued

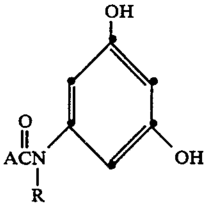

| No. | R | A | phys. constant |
|---|---|---|---|
| 1.032 | $-CH_3$ | 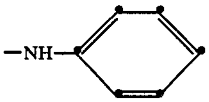 | m.p. >150° C. |
| 1.033 | H | 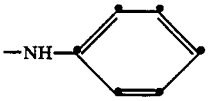 | m.p. 189–191° |
| 1.034 | H | $C_3H_7$ (i) | m.p. >220° C. (decomp.) (.½ Dioxan) |
| 1.035 | $CH_3$ | $C_3H_7$ (i) | m.p. >170° C. (decomp.) |
| 1.036 | $CH_3$ | $CH_2OCH_3$ | m.p. 170° C. (decomp.) |
| 1.037 | H | 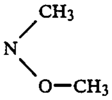 | |
| 1.038 | $CH_3$ | 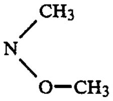 | |
| 1.039 | H | $CF_3$ | |
| 1.040 | H | $CH_2OCH_3$ | |

H.2 PREPARATION OF COMPOUNDS OF FORMULA II

H.2.1. N-isopropyl-N'-(cyclohexane-3,5-dion-1-yl)-urea

A solution of 0.1 mole (154 g of the compound obtainable in accordance with Example H.1.1) of N-isopropyl-N'-(3,5-dihydroxyphenyl)-urea in 440 ml of 1N NaOH is hydrogenated for 18 hours at 60°-65° C./10 bar in the presence of 30 g of Ra—Ni—$H_2O$. After filtering off the catalyst, the filtrate is acidified to pH 1 with HCl and cooled to 5° C. whereupon the product precipitates.

After filtering off the product with suction, it is rinsed with water and dried at 60° C./0.1 bar.

76 g (90%) of the title compound of formula

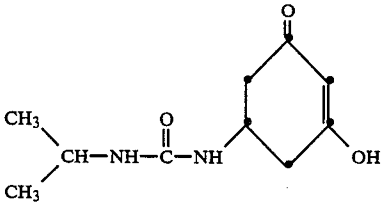

are isolated in the form of crystals having a melting point of >100° C. (decomposition) (Compound No. 2.004).

H.2.2. N-isopropyl-N'-methyl-N'-(cyclohexane-3,5-dion-1-yl)-urea

Analogously to Example H.2.1., there are obtained from 0.37 mole (100 g of compound 1.022 obtainable in accordance with Example H.1.2) of N-isopropyl-N'-methyl-N'-(3,5-dihydroxyphenyl)-urea, by hydrogenation, 58.2 g of the title compound of formula

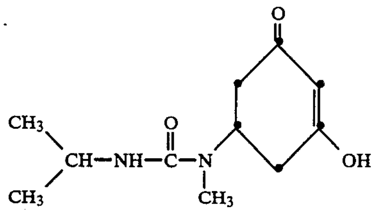

in the form of crystals having a melting point of 93°-95° C. (slow decomposition) (Compound No. 2.022).

H.2.3. 1-acetamido-cyclohexane-3,5-dione

A solution of 16.7 g (0.1 mole) of 5-acetamidoresorcinol in 110 ml of 0.1N NaOH is hydrogenated for 50 hours at 60°-65° C./10 bar in the presence of 10 g of Ra—Ni—$H_2O$. After filtering off the catalyst and acidifying the aqueous solution, the solution is concentrated to dryness at 50° C. 200 ml of ethanol and 0.1 ml of concentrated sulphuric acid are added to the residue, and the sodium chloride which precipitates is separated off and the filtrate is again concentrated to dryness. The residue is taken up in 200 ml of tetrahydrofuran and 10 ml of 1N hydrochloric acid, the whole is left at room temperature for 15 hours and the resulting suspension is dried over a molecular sieve and, after separating off the molecular sieve, is again concentrated to dryness.

11.5 g (68%) of the title compound of formula

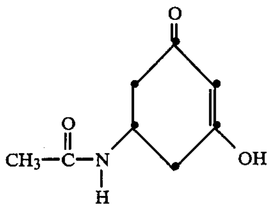

are obtained in the form of crystals having a melting point of 181°-183° C. (Compound No. 2.011).

The compounds in Table 2 can be obtained in an analogous manner.

TABLE 2

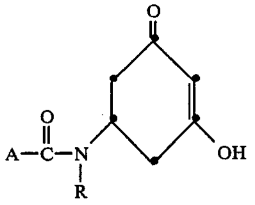

| No. | R | A | phys. data |
|---|---|---|---|
| 2.001 | H | $NHCH_3$ | solid |
| 2.002 | H | $NHC_2H_5$ | |
| 2.003 | H | $NHC_3H_7$ | |
| 2.004 | H | $NHC_3H_7$ (i) | >100° decomp. |
| 2.005 | H | $NHC_4H_9$ (n) | |
| 2.006 | H | $NHC_4H_9$ (t) | >180° decomp. |
| 2.007 | H | $OCH_3$ | m.p. 146-150° |
| 2.008 | H | $OC_2H_5$ | m.p. 172-174° |
| 2.009 | H | $OC_3H_7$ | m.p. 156-160° |
| 2.010 | H | $OC_3H_7$ (i) | |
| 2.011 | H | $CH_3$ | m.p. 181-183 |
| 2.012 | H | $C_2H_5$ | |
| 2.013 | H | $C_4H_9$ (n) | |
| 2.014 | H | $N(CH_3)_2$ | >180° decomp. |
| 2.015 | H | $N(C_2H_5)_2$ | |
| 2.016 | H | 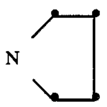 | >190° decomp. |
| 2.017 | H | 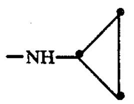 | |
| 2.018 | H | 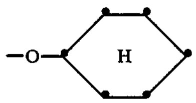 | |
| 2.019 | H | 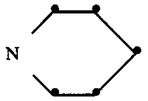 | |

TABLE 2-continued

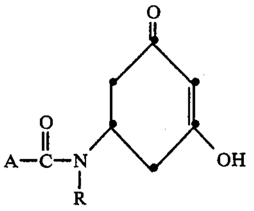

| No. | R | A | phys. data |
|---|---|---|---|
| 2.020 | $CH_3$ | $NHCH_3$ | solid |
| 2.021 | $CH_3$ | $N(CH_3)_2$ | |
| 2.022 | $CH_3$ | $NHC_3H_7$ (i) | m.p. 93-95° |
| 2.023 | $CH_3$ | $-OCH_3$ | |
| 2.024 | $CH_3$ | $-OC_3H_7$ (i) | |
| 2.025 | $CH_3$ | $CH_3$ | solid |
| 2.026 | $CH_3$ | $C_2H_5$ | |
| 2.027 | H | 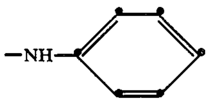 | m.p. >188° decomp. |
| 2.028 | H | 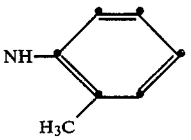 | solid |
| 2.029 | H | 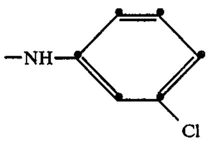 | |
| 2.030 | H | 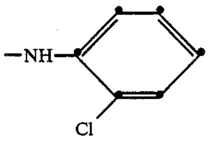 | m.p. 170° decomp. |
| 2.031 | H | 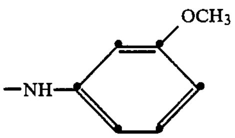 | solid |
| 2.032 | H | 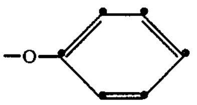 | |
| 2.033 | H | 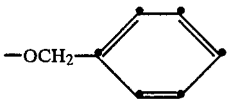 | m.p. 180° decomp. |
| 2.034 | H | 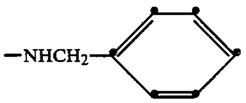 | |
| 2.035 | H | 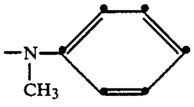 | |

TABLE 2-continued

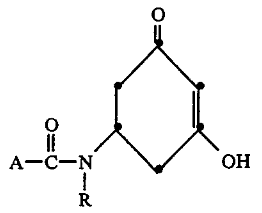

| No. | R | A | phys. data |
|---|---|---|---|
| 2.036 | $C_2H_5$ | $-NHCH_3$ | |
| 2.037 | $C_2H_5$ | $-N(CH_3)_2$ | |
| 2.038 | $C_3H_7$ (i) | $-NHCH_3$ | |
| 2.039 | H | $C_3H_7$ (i) | m.p. 204° C. |
| 2.040 | $CH_3$ | $C_3H_7$ (i) | |
| 2.041 | $CH_3$ | $CH_2-O-CH_3$ | |
| 2.042 | H | 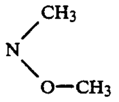 | |
| 2.043 | $CH_3$ | 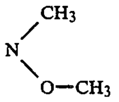 | |
| 2.044 | H | $CF_3$ | |
| 2.045 | H | $CH_2-O-CH_3$ | |

H.3.1. N,N-dimethyl-N'-(3-propionyloxy-cyclohex-3-en-5-on-1-yl)-urea 6.4 ml (71 mmoles) of propionic acid chloride are added while cooling at 20°-25° C. to a solution of 13.5 g (68 mmoles) of N,N-dimethyl-N'-(cyclohexane-3,5-dion-1-yl)-urea in 10.5 ml of triethylamine and 70 ml of ethyl acetate and then the whole is stirred for 15 hours at room temperature. The precipitated triethylamine hydrochloride is then filtered off and the filtrate is concentrated to dryness.

16.8 g (97%) of the title compound of formula

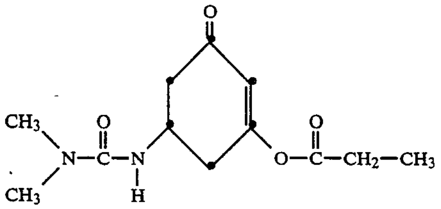

are isolated in the form of a wax-like solid having a melting point of 69°-74° C.

H.3.2. N-phenyl-N'-(3-methoxycyclohex-3-en-5-on-1-yl)-urea 30.7 ml (0.22 mole) of triethylamine are added to a suspension of 34 g (0.2 mole) of 3-methoxycyclohex-3-en-5-onecarboxylic acid in 500 ml of toluene, whereupon a clear solution forms. 21.5 ml (0.22 mole) of chloroformic acid are added dropwise to this solution at 0°-5° C. The whole is subsequently stirred for 1 hour at 0°-5° C. and then a solution of 16.25 g (0.25 mole) of sodium azide in 100 ml of water is added dropwise to the resulting suspension. The whole is again stirred at 0°-5° C. for one hour and then 200 ml of toluene are added.

The organic phase is washed with 200 ml of sodium hydrogen carbonate solution (50%) and dried over a molecular sieve (4Å). After removing the molecular sieve, 20 ml (0.22 mole) of aniline are added. The solution is then slowly heated to 90° C. Beyond 80° C., nitrogen begins to evolve. The solution is left for 2 hours at 90° C. and then the product is precipitated by adding hexane.

31 g (60%) of the title compound of formula

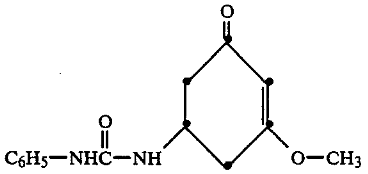

are isolated in the form of crystals having a melting point of 183°-185° C.

H.3.3. N-phenyl-N'-(cyclohexane-3,5-dion-1-yl)-urea 30 g of N-phenyl-N'-(3-methoxycyclohex-3-en-5-on-1-yl)-urea are stirred for 12 hours at room temperature in 230 ml of tetrahydrofuran, 11.5 ml of water and 1 ml of 37% hydrochloric acid. The whole is then concentrated to dryness under a water-jet vacuum and the residue is triturated with diethyl ether, filtered off with suction and dried.

28 g (98.9%) of the title compound of formula

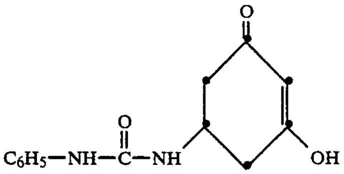

are isolated in the form of crystals having a melting point of 188° C. (decomposition).

H.4 PREPARATION OF COMPOUNDS OF FORMULA I

H.4.1. 5-(N,N-dimethylureido)-2-propionyl-cyclohexane-1,3-dione

A solution of 12.7 g (50 mmoles) of N,N-dimethyl-N'-(3-propionyloxycyclohex-3-en-5-on-1-yl)-urea in 100 ml of dichloroethane is stirred for 15 hours at room temperature together with 6.1 g (50 mmoles) of 4-dimethylaminopyridine. The whole is then neutralised with 0.5N hydrochloric acid (100 ml) and the organic phase is dried over $MgSO_4$ and concentrated to dryness.

8.2 g (64.6%) of the title compound of formula

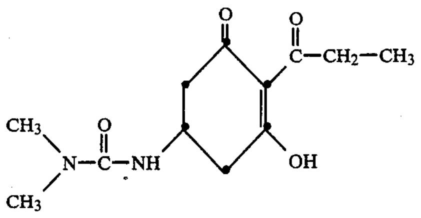

are isolated in the form of crystals having a melting point of 136°-138° C. (Compound No. 4.029).

H.4.2.
N-isopropyl-N'-[4-(4-chloro-2-nitrobenzoyl)-cyclohexane-3,5-dion-1-yl]-urea 8.8 g (40 mmoles) of 4-chloro-2-nitrobenzoyl chloride are added dropwise, while cooling, to a solution of 140 mmoles of N-isopropyl-N'-(3-hydroxycyclohex-3-en-5-on-1-yl)-urea in 80 ml of dichloromethane and 23 ml (0.16 mole) of triethylamine and then the whole is stirred for 1 hour at room temperature. 1 ml of acetone cyanohydrin is then added and the whole is stirred for a further 15 hours at room temperature. The reaction mixture is concentrated by evaporation and stirred with 400 ml of 0.5N hydrochloric acid. The precipitated product is separated off, washed with water and dried. The crude yield is 174 g. For purification, the product is converted into the sodium salt and precipitated again by adding acid.

7.7 g (53.5%) of the title compound of formula

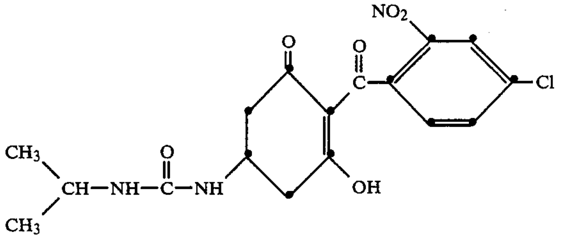

are isolated in the form of crystals having a melting point of >160° C. (decomposition) (Compound No. 4.010).

The compounds in Tables 3 and 4 can be obtained in an analogous manner.

TABLE 3

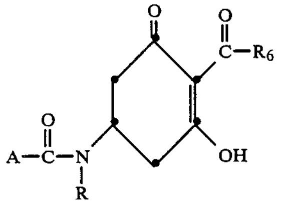

| No. | R | A | $R_6$ | physical data |
|---|---|---|---|---|
| 3.001 | H | $NHCH_3$ | $-C_3H_7$ | |
| 3.002 | H | $NHCH_3$ | 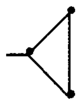 | |
| 3.003 | H | $NHC_2H_5$ | $-C_2H_5$ | |
| 3.004 | H | $NHC_2H_5$ | $-C_3H_7$ | |
| 3.005 | H | $NHC_3H_7$ (i) | $-C_2H_5$ | m.p. 188-190° C. |
| 3.006 | H | $NHC_3H_7$ (i) | $-C_3H_7$ | |
| 3.007 | H | $NHC_3H_7$ (i) | $-C_4H_9$ | |
| 3.008 | H | $NHC_3H_7$ (n) | $-C_3H_7$ (i) | |
| 3.009 | H | $NHC_4H_9$ (n) | $-CH_3$ | |
| 3.010 | H | $NHC_4H_9$ (n) | $-C_2H_5$ | |
| 3.011 | H | $NHC_4H_9$ (t) | $-C_2H_5$ | m.p. 174-175° C. |
| 3.012 | H | $NHC_4H_9$ (t) | $-C_3H_7$ | m.p. 141-143° C. |
| 3.013 | H | $NHC_4H_9$ (t) | 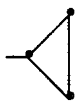 | m.p. 195-196° C. |
| 3.014 | H | $NHC_3H_7$ (i) | 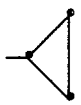 | m.p. 208-209° C. |
| 3.015 | H | $OCH_3$ | $-C_2H_5$ | |
| 3.016 | H | $OCH_3$ | $-C_4H_9$ | |
| 3.017 | H | $OC_2H_5$ | $-C_2H_5$ | |
| 3.018 | H | $OC_2H_5$ | $-C_3H_7$ | m.p. 102-104° C. |
| 3.019 | H | $OC_3H_7$ | $-CH_3$ | |
| 3.020 | H | $OC_3H_7$ (i) | $-C_2H_5$ | |

TABLE 3-continued
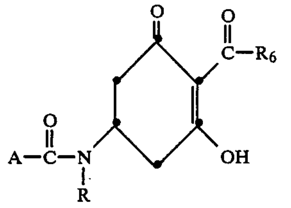
| No. | R | A | $R_6$ | physical data |
|---|---|---|---|---|
| 3.021 | H | $C_3H_7$ (i) | 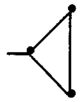 | |
| 3.022 | H | $CH_3$ | $C_2H_5$ | m.p. 159–161° C. |
| 3.023 | H | $CH_3$ | $C_3H_7$ | m.p. 124–126° C. |
| 3.024 | H | $CH_3$ | 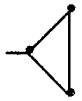 | m.p. 148–150° C. |
| 3.025 | H | $C_2H_5$ | 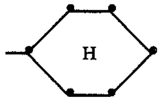 | |
| 3.026 | H | $C_2H_5$ | $CH_3$ | |
| 3.027 | H | $C_4H_9$ | $CH_3$ | |
| 3.028 | H | $C_4H_9$ | $C_2H_5$ | |
| 3.029 | H | $N(CH_3)_2$ | $C_2H_5$ | m.p. 136–138° C. |
| 3.030 | H | $N(CH_3)_2$ | $C_3H_7$ | m.p. 114–117° C. |
| 3.031 | H | $N(CH_3)_2$ | $C_6H_{13}$ | |
| 3.032 | H | $N(C_2H_5)_2$ | $C_2H_5$ | |
| 3.033 | H | $N(C_2H_5)_2$ | $C_3H_7$ | |
| 3.034 | H | $N(C_2H_5)_2$ | 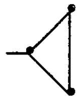 | |
| 3.035 | H | 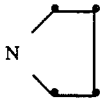 | $C_2H_5$ | |
| 3.036 | H | 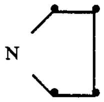 | $C_3H_7$ | |
| 3.037 | H | 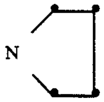 | 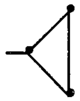 | m.p. 152–154° C. |
| 3.038 | H | 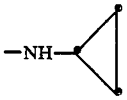 | $C_3H_7$ (i) | |
| 3.039 | H | 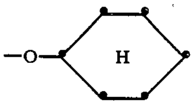 | $C_2H_5$ | |

TABLE 3-continued
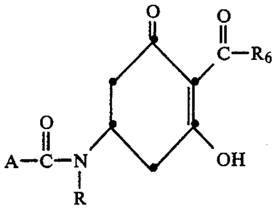
| No. | R | A | $R_6$ | physical data |
|---|---|---|---|---|
| 3.040 | H | 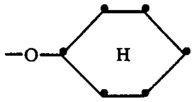 | 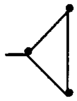 | |
| 3.041 | H | 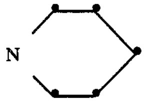 | $C_2H_5$ | |
| 3.042 | $CH_3$ | $NHCH_3$ | $C_2H_5$ | |
| 3.043 | $CH_3$ | $N(CH_3)_2$ | $C_2H_5$ | |
| 3.044 | $CH_3$ | $N(CH_3)_2$ | $C_3H_7$ | |
| 3.045 | $CH_3$ | $N(CH_3)_2$ | 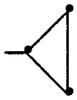 | |
| 3.046 | $CH_3$ | $NHC_3H_7$ (i) | $C_2H_5$ | |
| 3.047 | $CH_3$ | $NHC_3H_7$ (i) | 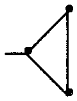 | m.p. 145–147° C. |
| 3.048 | $CH_3$ | $NHC_3H_7$ (i) | $CH_3$ | |
| 3.049 | $CH_3$ | $OCH_3$ | $C_2H_5$ | |
| 3.050 | $CH_3$ | $OCH_3$ | $C_3H_7$ | |
| 3.051 | $CH_3$ | $—OC_3H_7$ (i) | $C_2H_5$ | |
| 3.052 | $CH_3$ | $—OC_3H_7$ (i) | 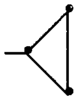 | |
| 3.053 | $CH_3$ | $CH_3$ | $C_2H_5$ | oil |
| 3.054 | $CH_3$ | $CH_3$ | 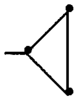 | |
| 3.055 | $CH_3$ | $CH_3$ | $C_3H_7$ | |
| 3.056 | $CH_3$ | $C_2H_5$ | $C_2H_5$ | |
| 3.057 | $CH_3$ | $C_2H_5$ | $C_3H_7$ | |
| 3.058 | H | 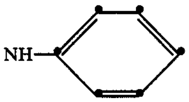 | $C_2H_5$ | |
| 3.059 | H | 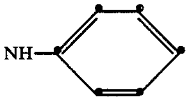 | 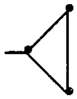 | m.p. 188–191° C. |

TABLE 3-continued
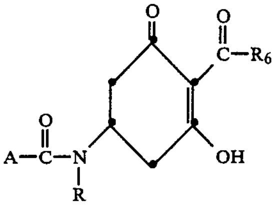
| No. | R | A | $R_6$ | physical data |
|---|---|---|---|---|
| 3.060 | H | 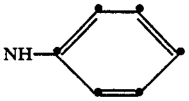 | $C_3H_7$ | m.p. 182-183° C. |
| 3.061 | H | 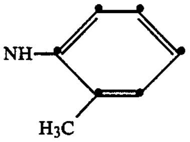 | $C_3H_7$ | m.p. >150° C. d. |
| 3.062 | H | 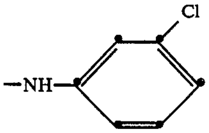 | $C_3H_7$ | m.p. >200° C. d. |
| 3.063 | H | 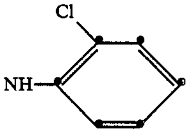 | $C_3H_7$ | |
| 3.064 | H | 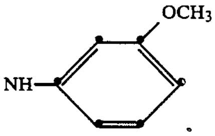 | $C_2H_5$ | |
| 3.065 | H | 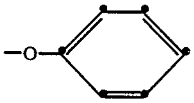 | $C_2H_5$ | |
| 3.066 | H | 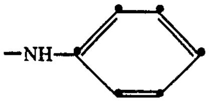 | $CH_3$ | m.p. 205° C. d. |
| 3.067 | H | 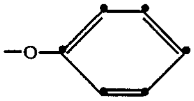 | 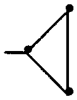 | |
| 3.068 | H | 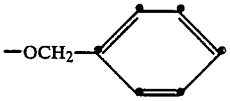 | $C_2H_5$ | |
| 3.069 | H | 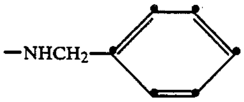 | $C_2H_5$ | |

TABLE 3-continued

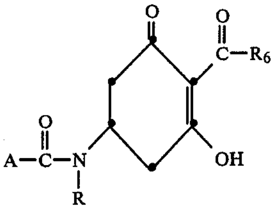

| No. | R | A | $R_6$ | physical data |
|---|---|---|---|---|
| 3.070 | H | 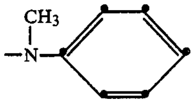 | $C_2H_5$ | |
| 3.071 | $C_2H_5$ | $NHCH_3$ | $C_2H_5$ | |
| 3.072 | $C_2H_5$ | $NHCH_3$ | $C_3H_7$ | |
| 3.073 | $C_2H_5$ | $NHCH_3$ | 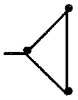 | |
| 3.074 | $C_2H_5$ | $N(CH_3)_2$ | $C_2H_5$ | |
| 3.075 | $C_3H_7$ (i) | $NHCH_3$ | $C_2H_5$ | |
| 3.076 | $C_3H_7$ (i) | $NHCH_3$ | $C_3H_7$ | |
| 3.077 | H | $C_3H_7$ (i) | $C_3H_7$ (n) | m.p. 169–170° C. |
| 3.078 | H | $C_3H_7$ (i) | $C_2H_5$ | m.p. 210–212° C. |
| 3.079 | H | $C_3H_7$ (i) | 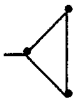 | m.p. 202–204° C. |
| 3.080 | H | $CH_2OCH_3$ | $C_3H_7$ (n) | |
| 3.081 | H | $CF_3$ | 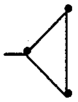 | |
| 3.082 | H | 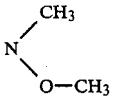 | $C_2H_5$ | |

TABLE 4

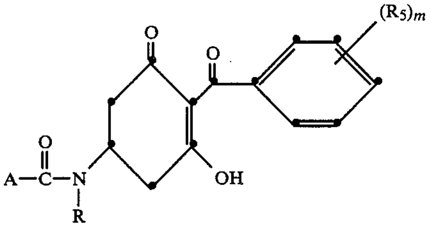

| No. | R | A | $(R_5)_m$ | physical data |
|---|---|---|---|---|
| 4.001 | H | $NHCH_3$ | 2-Cl | |
| 4.002 | H | $NHCH_3$ | 2,4-$Cl_2$ | |
| 4.003 | H | $NHCH_3$ | 2-$NO_2$ | |
| 4.004 | H | $NHC_2H_5$ | 2-$CF_3$ | |
| 4.005 | H | $NHC_2H_5$ | 2,4-$Cl_2$ | |
| 4.006 | H | $NHC_3H_7$ | 2-Cl | |
| 4.007 | H | $NHC_3H_7$ (i) | H | |
| 4.008 | H | $NHC_3H_7$ (i) | 2-Cl | |
| 4.009 | H | $NHC_3H_7$ (i) | 2,4-$Cl_2$ | m.p. 113–116° C. |
| 4.010 | H | $NHC_3H_7$ (i) | 2-$NO_2$,4-Cl | m.p. >160° C. (decomp.) |
| 4.011 | H | $NHC_3H_7$ (i) | 2-$CH_3$ | |

TABLE 4-continued

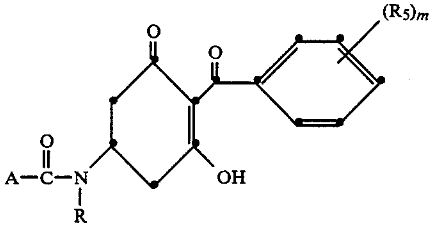

| No. | R | A | $(R_5)_m$ | physical data |
|---|---|---|---|---|
| 4.012 | H | $NHC_3H_7$ (i) | 2-$NO_2$ | |
| 4.013 | H | $NHC_3H_7$ (i) | 2-$OCH_3$ | |
| 4.014 | H | $NHC_4H_9$ (n) | 3-$OCH_3$ | |
| 4.015 | H | $NHC_4H_9$ (n) | 4-$CH_3$ | |
| 4.016 | H | $NHC_4H_9$ (n) | 2,4-$Cl_2$ | |
| 4.017 | H | $NHC_4H_9$ (t) | 2,4-$Cl_2$ | m.p. 154–156° C. |
| 4.018 | H | $NHC_4H_9$ (t) | 2-$NO_2$ | m.p. 170° C. d. |
| 4.019 | H | $NHC_4H_9$ (t) | H | m.p. 148–150° C. |
| 4.020 | H | $NHC_4H_9$ (t) | 3-$NO_2$ | |
| 4.021 | H | $NHC_4H_9$ (t) | 2-$NO_2$,4-Cl | m.p. >172° C. (decomp.) |
| 4.022 | H | $OCH_3$ | 2,4 $Cl_2$ | |
| 4.023 | H | $OCH_3$ | H | |
| 4.024 | H | $OC_2H_5$ | 2-$NO_2$,4-Cl | |
| 4.025 | H | $OC_2H_5$ | 2,4-$Cl_2$ | m.p. 100–103° C. |
| 4.026 | H | $OC_3H_7$ (i) | 2,4-$Cl_2$ | |
| 4.027 | H | $OC_3H_7$ (i) | 2-$NO_2$ | |
| 4.028 | H | $OC_3H_7$ (i) | H | |
| 4.029 | H | $OC_3H_7$ | 2,4-$Cl_2$ | |
| 4.030 | H | $OC_3H_7$ | 2-$NO_2$ | |
| 4.031 | H | $CH_3$ | 2,4-$Cl_2$ | m.p. 152–153° C. |
| 4.032 | H | $CH_3$ | 2-$NO_2$ | |
| 4.033 | H | $CH_3$ | H | |
| 4.034 | H | $CH_2CH_3$ | 2-$NO_2$,4-Cl | |
| 4.035 | H | $CH_2CH_3$ | 4-$OCH_3$ | |
| 4.036 | H | $CH_2CH_3$ | 2-F, 6-Cl | |
| 4.037 | H | $C_4H_9$ (n) | 2-Cl | |
| 4.038 | H | $N(CH_3)_2$ | 2,4-$Cl_2$ | m.p. 90–95° C. |
| 4.039 | H | $N(CH_3)_2$ | 2-$NO_2$ | |
| 4.040 | H | $N(CH_3)_2$ | H | |
| 4.041 | H | $N(C_2H_5)_2$ | 2-$NO_2$,4Cl | |
| 4.042 | H | $N(C_2H_5)_2$ | 2Cl | |
| 4.043 | H | $N(C_2H_5)_2$ | 4-Br | |
| 4.044 | H | 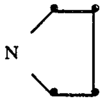 | 2,4 $Cl_2$ | m.p. 93–96° C. |
| 4.045 | H | 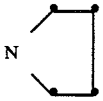 | 2-$NO_2$ | |
| 4.046 | H | 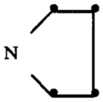 | 3-$CF_3$ | |
| 4.047 | H | 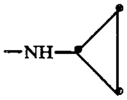 | 2-$NO_2$ | |
| 4.048 | H | 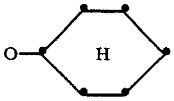 | H | |

TABLE 4-continued
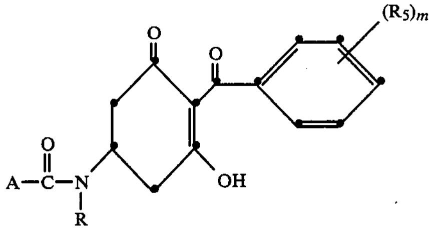
| No. | R | A | $(R_5)_m$ | physical data |
|---|---|---|---|---|
| 4.049 | H | 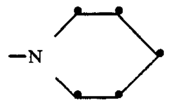 | 2-Cl | |
| 4.050 | H | 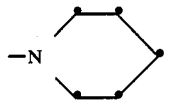 | $2-NO_2$ | |
| 4.051 | $CH_3$ | $NHCH_3$ | $2-NO_2$ | |
| 4.052 | $CH_3$ | $NHCH_3$ | $2,4-Cl_2$ | |
| 4.053 | $CH_3$ | $NHC_3H_7$ (i) | $2-NO_2$ | |
| 4.054 | $CH_3$ | $NHC_3H_7$ (i) | H | |
| 4.055 | $CH_3$ | $NHC_3H_7$ (i) | $2-NO_2,4-Cl$ | |
| 4.056 | $CH_3$ | $NHC_3H_7$ (i) | $2,4\ Cl_2$ | |
| 4.057 | $CH_3$ | $NHC_3H_7$ (i) | $3-OCH_3$ | |
| 4.058 | $CH_3$ | $-OCH_3$ | $2-NO_2$ | |
| 4.059 | $CH_3$ | $-OCH_3$ | 2-Cl | |
| 4.060 | $CH_3$ | $-OC_3H_7$ (i) | $2,4-Cl_2$ | |
| 4.061 | $CH_3$ | $CH_3$ | $2-NO_2$ | |
| 4.062 | $CH_3$ | $CH_3$ | H | |
| 4.063 | $CH_3$ | $CH_3$ | $2-CF_3$ | |
| 4.064 | $CH_3$ | $C_2H_5$ | $2,4-Cl_2$ | |
| 4.065 | H | 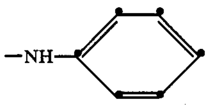 | $2-NO_2$ | |
| 4.066 | H | 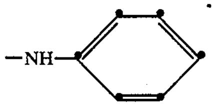 | $2,4-Cl_2$ | m.p. 174–175° C. |
| 4.067 | H | 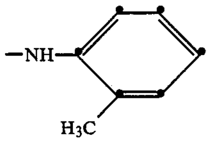 | 2-Cl | |
| 4.068 | H | 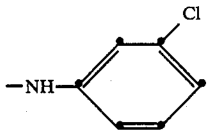 | H | |
| 4.069 | H | 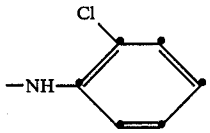 | $4-OCH_3$ | |
| 4.070 | H | 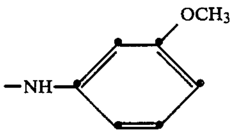 | $2-NO_2,4-Cl$ | |

TABLE 4-continued

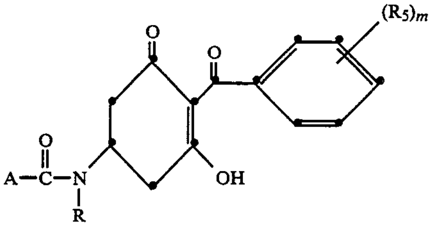

| No. | R | A | $(R_5)_m$ | physical data |
|---|---|---|---|---|
| 4.071 | H | 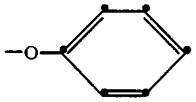 | H | |
| 4.072 | H | 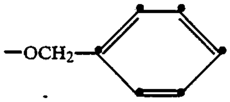 | 2,4-$Cl_2$ | |
| 4.073 | H | 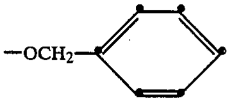 | H | |
| 4.074 | H | 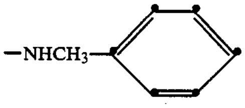 | 2,4-$Cl_2$ | |
| 4.075 | $CH_3$ | 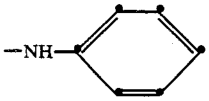 | 2-$NO_2$ | |
| 4.076 | $C_2H_5$ | $-NHCH_3$ | 2,4-$Cl_2$ | |
| 4.077 | $C_2H_5$ | $-NHCH_3$ | H | |
| 4.078 | $C_2H_5$ | $-NHCH_3$ | 2-$NO_2$ | |
| 4.079 | $C_2H_5$ | $N(CH_3)_2$ | 2,4-$Cl_2$ | |
| 4.080 | $C_2H_5$ | $N(CH_3)_2$ | 2-$NO_2$ | |
| 4.081 | $C_2H_5$ | $N(CH_3)_2$ | H | |
| 4.082 | $C_3H_7$ (i) | $NHCH_3$ | 2,4-$Cl_2$ | m.p. 127-130° C. |
| 4.083 | $C_3H_7$ (i) | $NHCH_3$ | 2-$NO_2$ | |
| 4.084 | $C_3H_7$ (i) | $NHCH_3$ | 2-$NO_2$,4-Cl | |
| 4.085 | $C_3H_7$ (i) | $NHCH_3$ | H | |
| 4.086 | H | $N(CH_3)_2$ | 2-Cl, 4-$SCH_3$ | |
| 4.087 | H | $N(CH_3)_2$ | 2-Cl, 4-SO$-CH_3$ | |
| 4.088 | H | $(CH_3)_2$ | 2-Cl, 3-$SO_2-CH_3$ | |
| 4.089 | H | $N(CH_3)_2$ | 2-$SCH_3$, 4-Cl | |
| 4.090 | H | $N(CH_3)_2$ | 2-SO$-CH_3$, 4-Cl | |
| 4.091 | H | $N(CH_3)_2$ | 2-$SO_2-CH_3$, 4-Cl | |
| 4.092 | $CH_3$ | $N(CH_3)_2$ | 4-$SO_2-CH_3$, 2-Cl | |
| 4.093 | $CH_3$ | $N(CH_3)_2$ | 2-$SO_2-CH_3$, 4-Cl | |
| 4.094 | H | $CH_3$ | 2-$SO_2-CH_3$, 4-Cl | |
| 4.095 | H | $CH_3$ | 4-$SO_2-CH_3$, 2-Cl | |
| 4.096 | H | 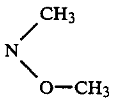 | 2,4-$Cl_2$ | |

TABLE 4-continued

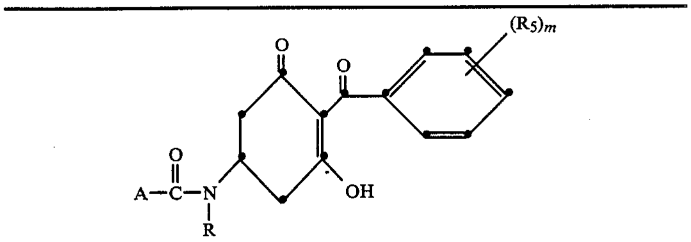

| No. | R | A | $(R_5)_m$ | physical data |
|---|---|---|---|---|
| 4.097 | H | 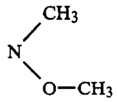 | 2-Cl, 4-$SO_2$—$CH_3$ | |
| 4.098 | H | $CH_2$—O—$CH_3$ | 2-$SO_2$—$CH_3$, 4-Cl | |
| 4.099 | H | $CF_3$ | 2,4-$Cl_2$ | |
| 4.100 | $CH_3$ | $CF_3$ | 2-Cl, 4-$SO_2$—$CH_3$ | |
| 4.101 | H | $C_3H_7$ (i) | 2,4-$Cl_2$ | m.p. 133-134° C. |
| 4.102 | H | $NH(C_3H_7)$ (i) | 2,5-$Cl_2$ | m.p. 162-164° C. |
| 4.103 | H | $CH_3$ | 2,5-$Cl_2$ | m.p. 136-138° C. |

H.5 PREPARATION OF THE OXIME ETHERS OF FORMULA I

H.5.1. 5-(N,N-dimethylureido)-2-(1-ethoxyiminobutyl)-cyclohexane-1,3-dione 3.05 g (12 mmoles) of 5-(N,N-dimethylureido)-2-propionyl-cyclohexane-1,3-dione, 1.3 g (13 mmoles) of 0-ethylhydroxylamine hydrochloride and 2 ml (13 mmoles) of 1,8-diazabicyclo(5.4.0)undec-7-ene in 24 ml of ethanol are stirred for 15 hours at room temperature. The reaction mixture is then diluted with 200 ml of ethyl acetate, adjusted to pH 1-2 with 1N hydrochloric acid while cooling at 0°-5° C., washed several times with water and, after being dried over $MgSO_4$, is concentrated to dryness by evaporation. The resulting crude product is purified over silica gel using ethyl acetate/ethanol (10:1).

2.4 g (67.3%) of the title compound of formula

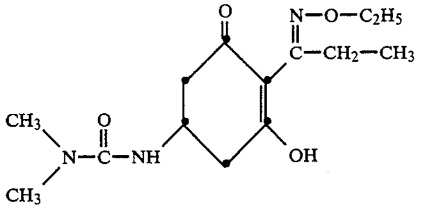

are isolated in the form of wax-like crystals having a melting point of 94°-97° C. (Compound No. 5.028).

The compounds of Table 5 can be obtained in an analogous manner.

TABLE 5

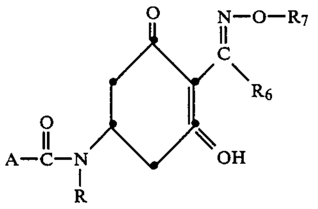

| No. | R | A | $R_6$ | $R_7$ | physical data |
|---|---|---|---|---|---|
| 5.001 | H | $NHCH_3$ | $C_3H_7$ | $C_2H_5$ | |
| 5.002 | H | $NHC_2H_5$ | $C_2H_5$ | $C_2H_5$ | |
| 5.003 | H | $NHC_2H_5$ | $C_3H_7$ | $CH_2CH$=CHCl | |
| 5.004 | H | $NHC_3H_7$ (i) | $C_2H_5$ | $C_2H_5$ | m.p. 153-154° C. |
| 5.005 | H | $NHC_3H_7$ (i) | $C_2H_5$ | $CH_2CH$=CHCl | |
| 5.006 | H | $NHC_3H_7$ (i) | $C_3H_7$ | $C_2H_5$ | |
| 5.007 | H | $NHC_3H_7$ (i) | $C_4H_9$ | $CH_3$ | |
| 5.008 | H | $NHC_3H_7$ (n) | $C_3H_7$ (i) | $C_2H_5$ | |
| 5.009 | H | $NHC_4H_9$ (n) | $CH_3$ | $C_4H_9$ (n) | |
| 5.010 | H | $NHC_4H_9$ (n) | $C_2H_5$ | $C_2H_5$ | |
| 5.011 | H | $NHC_4H_9$ (t) | $C_2H_5$ | $C_2H_5$ | m.p. 121-124° C. |
| 5.012 | H | $NHC_4H_9$ (t) | $C_2H_5$ | $CH_2CH$=CHCl | |
| 5.013 | H | $NHC_4H_9$ (t) | $C_3H_7$ | $C_2H_5$ | m.p. 123-126° C. |
| 5.014 | H | $NHC_4H_9$ (t) | $C_3H_7$ | $CH_2CH$=$CH_2$ | |
| 5.015 | H | $OCH_3$ | $C_2H_5$ | $C_2H_5$ | |
| 5.016 | H | $OCH_3$ | $C_4H_9$ | $C_2H_5$ | |
| 5.017 | H | $OC_2H_5$ | $C_2H_5$ | $CH_2CH$=CHCl | |

TABLE 5-continued

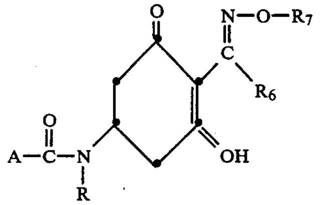

| No. | R | A | $R_6$ | $R_7$ | physical data |
|---|---|---|---|---|---|
| 5.018 | H | $OC_2H_5$ | $C_3H_7$ | $C_2H_5$ | wax |
| 5.019 | H | $OC_2H_5$ | $C_3H_7$ | $CH_2C{\equiv}CH$ | |
| 5.020 | H | $OC_3H_7$ | $CH_3$ | $C_4H_9$ (n) | |
| 5.021 | H | $OC_3H_7$ (i) | $C_2H_5$ | $C_2H_5$ | |
| 5.022 | H | $CH_3$ | $C_2H_5$ | $C_2H_5$ | wax |
| 5.023 | H | $CH_3$ | $C_2H_5$ | $CH_2CH{=}CHCl$ | |
| 5.024 | H | $CH_3$ | $C_3H_7$ | $C_2H_5$ | m.p. 111-113° C. |
| 5.025 | H | $C_2H_5$ | $CH_3$ | $C_2H_5$ | |
| 5.026 | H | $C_4H_9$ | $CH_3$ | $CH_2CH{=}CH_2$ | |
| 5.027 | H | $C_4H_9$ | $C_2H_5$ | $C_2H_5$ | |
| 5.028 | H | $N(CH_3)_2$ | $C_2H_5$ | $C_2H_5$ | m.p. 94-97° C. |
| 5.029 | H | $N(CH_3)_2$ | $C_3H_7$ | $CH_2CH{=}CHCl$ | cis/trans resin |
| 5.030 | H | $N(CH_3)_2$ | $C_3H_7$ | $CH_2CH{=}CHCl$ | trans |
| 5.031 | H | $N(CH_3)_2$ | $C_3H_7$ | $C_2H_5$ | m.p. 105-107° C. |
| 5.032 | H | $N(C_2H_5)_2$ | $C_2H_5$ | $C_2H_5$ | |
| 5.033 | H | $N(C_2H_5)_2$ | $C_3H_7$ | $C_2H_5$ | |
| 5.034 | H | 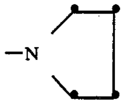 | $C_2H_5$ | $CH_2CH{=}CHCl$ | |
| 5.035 | H | 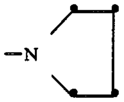 | $C_3H_7$ | $C_2H_5$ | |
| 5.036 | H | 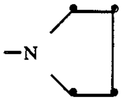 | $C_2H_5$ | $C_2H_5$ | |
| 5.037 | H | 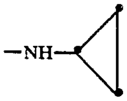 | $C_3H_7$ (i) | $C_2H_5$ | |
| 5.038 | H | 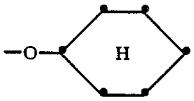 | $C_2H_5$ | $C_2H_5$ | |
| 5.039 | H | 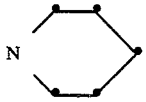 | $C_2H_5$ | $C_2H_5$ | |
| 5.040 | $CH_3$ | $NHCH_3$ | $C_2H_5$ | $CH_2CH{=}CHCl$ | |
| 5.041 | $CH_3$ | $N(CH_3)_2$ | $C_2H_5$ | $C_2H_5$ | |
| 5.042 | $CH_3$ | $N(CH_3)_2$ | $C_3H_7$ | $C_2H_5$ | |
| 5.043 | $CH_3$ | $NHC_3H_7$ (i) | $C_2H_5$ | $C_2H_5$ | |
| 5.044 | $CH_3$ | $NHC_3H_7$ (i) | $C_2H_5$ | $CH_2CH{=}CHCl$ | |
| 5.045 | $CH_3$ | $NHC_3H_7$ (i) | $CH_3$ | $C_4H_9$ (n) | |
| 5.046 | $CH_3$ | $OCH_3$ | $C_2H_5$ | $C_2H_5$ | |
| 5.047 | $CH_3$ | $OCH_3$ | $C_3H_7$ | $C_2H_5$ | |
| 5.048 | $CH_3$ | $OC_3H_7$ (i) | $C_2H_5$ | $C_2H_5$ | |
| 5.049 | $CH_3$ | $CH_3$ | $C_2H_5$ | $C_2H_5$ | oil |
| 5.050 | $CH_3$ | $CH_3$ | $C_2H_5$ | $CH_2CH{=}CHCl$ | |
| 5.051 | $CH_3$ | $CH_3$ | $C_3H_7$ | $C_2H_5$ | |
| 5.052 | $CH_3$ | $C_2H_5$ | $C_2H_5$ | $C_2H_5$ | |
| 5.053 | $CH_3$ | $C_2H_5$ | $C_3H_7$ | $C_2H_5$ | |

TABLE 5-continued
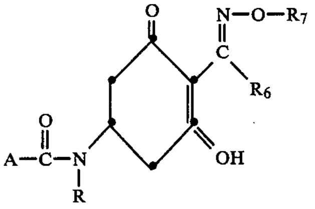
| No. | R | A | $R_6$ | $R_7$ | physical data |
|---|---|---|---|---|---|
| 5.054 | H | 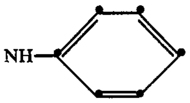 | $C_2H_5$ | $C_2H_5$ | |
| 5.055 | H | 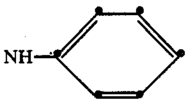 | $C_3H_7$ | $C_2H_5$ | m.p. 133–135° C. |
| 5.056 | H | 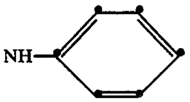 | $C_3H_7$ | $CH_2CH{=}CHCl$ | cis/trans m.p. 101–103° C. |
| 5.057 | H | 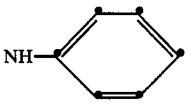 | $C_3H_7$ | $CH_2CH{=}CHCl$ | trans |
| 5.058 | H | 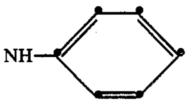 | $C_3H_7$ | $CH_3$ | m.p. 159° C. |
| 5.059 | H | 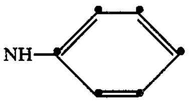 | $CH_3$ | $C_2H_5$ | m.p. 156° C. |
| 5.060 | H | 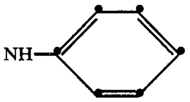 | $CH_3$ | $CH_2CH{=}CHCl$ | cis/trans m.p. 135° C. |
| 5.061 | H | 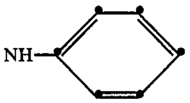 | $CH_3$ | $CH_2CH{=}CHCl$ | trans |
| 5.062 | H | 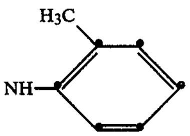 | $C_3H_7$ | $C_2H_5$ | m.p. 133–135° C. |
| 5.063 | H | 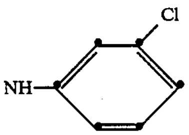 | $C_3H_7$ | $C_2H_5$ | m.p. 117–120° C. |

TABLE 5-continued

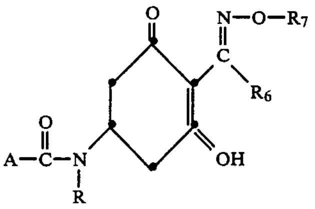

| No. | R | A | $R_6$ | $R_7$ | physical data |
|---|---|---|---|---|---|
| 5.064 | H | 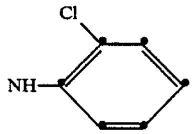 | $C_3H_7$ | $C_2H_5$ | |
| 5.065 | H | 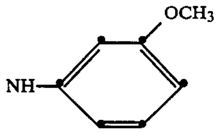 | $C_2H_5$ | $C_2H_5$ | |
| 5.066 | H | 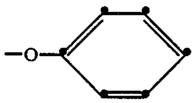 | $C_2H_5$ | $C_2H_5$ | |
| 5.067 | H | 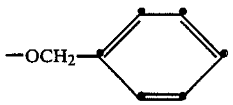 | $C_2H_5$ | $C_2H_5$ | |
| 5.068 | H | 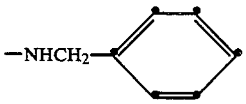 | $C_2H_5$ | $C_2H_5$ | |
| 5.069 | H | 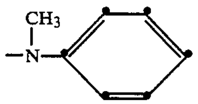 | $C_2H_5$ | $C_2H_5$ | |
| 5.070 | $C_2H_5$ | $NHCH_3$ | $C_2H_5$ | $C_2H_5$ | |
| 5.071 | $C_2H_5$ | $NHCH_3$ | $C_3H_7$ | $C_2H_5$ | |
| 5.072 | $C_2H_5$ | $N(CH_3)_2$ | $C_2H_5$ | $CH_2CH{=}CHCl$ | |
| 5.073 | $C_2H_5$ | $N(CH_3)_2$ | $C_2H_5$ | $C_2H_5$ | |
| 5.074 | $C_3H_7$ (i) | $NHCH_3$ | $C_2H_5$ | $C_2H_5$ | |
| 5.075 | $C_3H_7$ (i) | $NHCH_3$ | $C_2H_5$ | $CH_2CH{=}CHCl$ | |
| 5.076 | $C_3H_7$ (i) | $NHCH_3$ | $C_3H_7$ | $C_2H_5$ | |
| 5.077 | H | $C_3H_7$ (i) | $C_3H_7$ | $C_2H_5$ | m.p. 80-90° C. (wax) |
| 5.078 | H | $C_3H_7$ (i) | $C_2H_5$ | $C_2H_5$ | m.p. 105-107° C. |

EXAMPLE F.6: Formulation Examples

Example F.6.1: Formulation Examples for active ingredients of formula I (throughout, percentages are by weight)

| (a) Emulsifiable concentrates | (a) | (b) | (c) |
|---|---|---|---|
| a compound according to Preparatory Example 4 or 5 | 25% | 40% | 50% |
| calcium dodecylbenzenesulphonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |

-continued

| (a) Emulsifiable concentrates | (a) | (b) | (c) |
|---|---|---|---|
| xylene mixture | 70% | 25% | 20% |

Emulsions of any required concentration can be produced from such concentrates by dilution with water.

| (b) Solutions | (a) | (b) | (c) |
|---|---|---|---|
| a compound according to Preparatory Example 4 or 5 | 80% | 10% | 5% |
| ethylene glycol monomethyl ether | 20% | — | — |
| polyethylene glycol (mol. wt. 400) | — | 70% | — |
| N—methyl-2-pyrrolidone | — | 20% | 5% |

-continued

| (b) Solutions | (a) | (b) | (c) |
|---|---|---|---|
| epoxidised coconut oil | — | — | 90% |

These solutions are suitable for application in the form of micro-drops.

| (c) Granulates | (a) | (b) |
|---|---|---|
| a compound according to Preparatory Example 4 or 5 | 5% | 10% |
| kaolin | 94% | — |
| highly dispersed silicic acid | 1% | — |
| attapulgite | — | 90% |

The active ingredient is dissolved, the solution is sprayed onto the carrier, and the solvent is subsequently evaporated off in vacuo.

| (d) Dusts | (a) | (b) | (c) |
|---|---|---|---|
| a compound according to Preparatory Example 4 or 5 | 2% | 5% | 8% |
| highly dispersed silicic acid | 1% | 5% | 5% |
| talcum | 97% | — | 10% |
| kaolin | — | 90% | 77% |

Ready-for-use dusts are obtained by intimately mixing the carriers with the active ingredient.

| (e) Wettable powders | (a) | (b) |
|---|---|---|
| a compound according to Preparatory Example 4 or 5 | 20% | 60% |
| sodium lignosulphonate | 5% | 5% |
| sodium lauryl sulphate | 3% | 6% |
| octylphenol polyethylene glycol ether (7-8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (f) Extruder granulate | |
|---|---|
| a compound according to Preparatory Example 4 or 5 | 10% |
| sodium lignosulphonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| (g) Coated granulate | |
|---|---|
| a compound according to Preparatory Example 4 or 5 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| (h) Suspension concentrate | |
|---|---|
| a compound according to Preparatory Example 4 or 5 | 40% |
| ethylene glycol | 10% |
| nonylphenol polyethylene glycol ether (15 moles of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE B.7. Biological Examples

Example 7.1: Preemergence Herbicidal Action

Immediately after sowing seeds of the test plants in dishes in a greenhouse, the surface of the soil is treated with an aqueous active ingredient dispersion obtained from a 25% emulsion concentrate. Concentrations of 4 kg of active ingredient/hectare are used. The dishes are kept in the greenhouse at 22°-25° C. and 50-70% relative humidity and the test is evaluated after 3 weeks.

The herbicidal action is evaluated using a linear nine-stage assessment scheme in which 1 represents total destruction (100% herbicidal action) and 9 represents no action (test plant grows in the same way as the untreated reference).

The individual results are set out in Table 6.

TABLE 6

| | Preemergence herbicidal action at a rate of application of 4 kg/ha | | | |
|---|---|---|---|---|
| Comp. No. | Avena | Sinapis | Setaria | Stellaria |
| 5.056 | 5 | 9 | 1 | 9 |
| 5.055 | 1 | 9 | 1 | 9 |
| 5.059 | 4 | 9 | 1 | 9 |
| 4.038 | 3 | 1 | 1 | 1 |
| 5.062 | 4 | 9 | 1 | 9 |
| 3.029 | 3 | 8 | 1 | 1 |
| 3.030 | 2 | 9 | 1 | 4 |
| 5.028 | 1 | 9 | 1 | 9 |
| 5.063 | 2 | 9 | 1 | 9 |
| 4.009 | 2 | 4 | 1 | 1 |

Example 7.2: Postemergence Herbicidal Action (contact herbicide)

A number of weeds, both mono- and dicotyledonous, are sprayed postemergence in the 4- to 6-leaf stage with an aqueous active ingredient dispersion at a rate of 4 kg of test compound per hectare and kept at 24°-26° C. and 45-60% relative humidity. The test is evaluated 15 days later.

The compounds according to Preparatory Examples 4 and 5 exhibit good to very good herbicidal activity in this test.

Example 7.3: Herbicidal Action in Wild Rice (paddy rice)

The weeds *Echinochloa crus galli* and *Monocharia* vag., which occur in water, are sown in plastic beakers (surface: 60 $cm^2$; volume: 500 ml). After sowing, the beakers are filled with water up to the surface of the soil. 3 days after sowing, the water level is increased to slightly above the soil surface (3-5 mm). Application is effected 3 days after sowing by spraying the beakers with an aqueous emulsion of the test compounds. The rate of application corresponds to a concentration of 0.5 to 4 kg of active ingredient per hectare. The beakers are then kept in the greenhouse under optimum growth conditions for rice weeds, i.e. at 25°-30° C. and at high humidity.

The evaluation of the tests takes place 3 weeks after application.

The individual results are set out in Table 7.

TABLE 7

| Verb. Nr. | Echinochloa | Monocharia |
|---|---|---|
| 3.018 | 1 | 2 |
| 5.058 | 1 | 9 |
| 4.038 | 1 | 1 |
| 3.029 | 2 | 3 |
| 3.030 | 1 | 4 |
| 4.025 | 2 | 1 |
| 5.013 | 1 | 2 |
| 4.009 | 1 | 1 |

Example 7.4: Growth Inhibition of Tropical Cover Crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity. In this test a marked reduction in new growth of the plants treated with compounds according to Preparatory Examples 4 and 5 at rates of application of up to 3000 g/ha is observed, without damage being caused to the test plants.

Example 7.5: Growth Regulation of Soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of formula I until thoroughly wetted. The rate of application corresponds to up to 100 g a.i. per hectare. Evaluation is made about 5 weeks after application. Compared with untreated controls, the compounds according to the invention of Preparatory Examples 4 and 5 markedly increase the number and weight of the harvested siliques on the leading shoot.

Example 7.6: Growth Inhibition of Cereals

The cereal varieties summer barley (Hordeum vulgare) and summer rye (Secale) are sown in sterilised soil in plastic beakers in a greenhouse and watered as required. The cereal shoots are treated about 21 days after sowing with an aqueous spray mixture of a compound according to Preparatory Example 4 or 5. The concentration corresponds to up to 100 g of active ingredient per hectare. Evaluation of the growth of the cereals is made 21 days after application. A comparison with untreated controls shows that the new growth of the treated plants is reduced (60-90% of the controls) and that the diameter of the stalks has in some cases increased.

Example 7.7: Growth Inhibition of Grasses

Seeds of the grasses *Lolium perenne, Poa pratensis, Festuca ovina, Dactylis glomerata* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound according to Preparatory Example 4 or 5. The concentration of test compound corresponds to a rate of application of up to 500 g a.i. per hectare. The growth of the grasses is evaluated 21 days after application.

The compounds according to Preparatory Examples 4 and 5 effect a reduction in new growth in comparison with untreated controls.

I claim:

1. Compounds of formula I

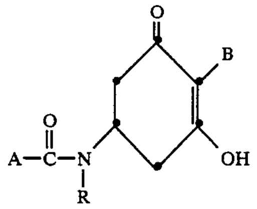

(I)

in which

R is hydrogen or $C_1$-$C_6$-alkyl,

A is $R_2$, $OR_3$ or $NR_3R_4$, $R_2$ is $C_1$-$C_6$ alkyl that is unsubstituted or is mono-substituted by $C_1$-$C_4$-alkoxy or mono- or poly-substituted by halogen, or is $C_3$-$C_6$-cycloalkyl, $R_3$ is $C_1$-$C_6$-alkyl or $C_3$-$C_6$-cycloalkyl, or is phenyl or benzyl each of which is unsubstituted or is mono-, di- or tri-substituted by $R_5$, $R_4$ is hydrogen, $C_1$-$C_6$-alkyl, $C_1$-$C_4$-alkoxy or $C_3$-$C_6$-cycloalkyl, B is one of the radicals

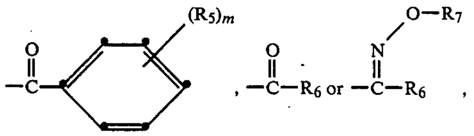

m is 0, 1, 2 or 3, $R_5$ is halogen, nitro, cyano, $C_1$-$C_4$-alkyl, $C_1$-$C_4$-alkoxy, $C_1$-$C_4$-alkylthio, $C_1$-$C_4$-haloalkyl, $C_1$-$C_4$-alkylsulphinyl or $C_1$-$C_4$-alkylsulphonyl, $R_6$ is $C_1$-$C_6$-alkyl or $C_3$-$C_6$-cycloalkyl, and $R_7$ is hydrogen, $C_1$-$C_6$-alkyl, $C_1$-$C_6$-haloalkyl, $C_3$-$C_6$-alkenyl, $C_3$-$C_6$-haloalkenyl or $C_3$-$C_6$-alkynyl, and salts of the compounds of formula I with acids, bases or complexformers.

2. Compounds of formula I according to claim 1, in which

R is hydrogen or $C_1$-$C_4$-alkyl,

A is $R_2$, $OR_3$ or $NR_3R_4$, $R_2$ is cyclopropyl, cyclopentyl or cyclohexyl, or is $C_1$–$C_4$-alkyl that is unsubstituted or is mono-substituted by $C_1$–$C_4$-alkoxy or mono- or poly-substituted by halogen, $R_3$ is $C_1$–$C_4$-alkyl, cyclopropyl, cyclopentyl or cyclohexyl, or is phenyl or benzyl each of which is unsubstituted or is mono- or di-substituted by $R_5$, $R_4$ is hydrogen, $C_1$–$C_4$-alkyl, methoxy, cyclopropyl, cyclopentyl or cyclohexyl, B is one of the radicals

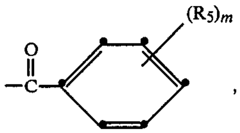 , 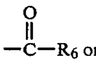 or 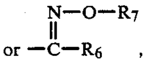 , m is 0, 1, 2 or 3, $R_5$ is fluorine, chlorine, bromine, nitro, cyano, $C_1$–$C_4$-alkyl, $C_1$–$C_4$-alkoxy, $C_1$–$C_4$-alkylthio, trifluoromethyl, $C_1$–$C_4$-alkylsulphinyl or $C_1$–$C_4$-alkylsulphonyl, $R_6$ is $C_1$–$C_4$-alkyl, cyclopropyl, cyclopentyl or cyclohexyl, and $R_7$ is hydrogen, $C_1$–$C_4$-alkyl, $C_1$–$C_4$-haloalkyl, $C_3$–$C_4$-alkenyl, $C_3$–$C_4$-haloalkenyl or $C_3$–$C_4$-alkynyl.

3. Compounds of formula I according to claim 1 in which

R is hydrogen or $C_1$–$C_3$-alkyl,

A is $R_2$, $OR_3$ or $NR_3R_4$, $R_2$ is $C_1$–$C_4$-alkyl, methoxymethyl or trifluoromethyl, $R_3$ is $C_1$–$C_4$-alkyl, cyclopropyl, cyclohexyl or benzyl, or is phenyl that is unsubstituted or is substituted by chlorine, methoxy or by methyl, $R_4$ is hydrogen, methyl, methoxy or ethyl, B is one of the radicals

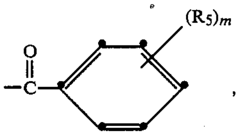 , 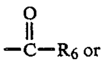 or 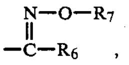 , m is 0, 1, 2 or 3, $R_5$ is fluorine, chlorine, bromine, nitro, methyl, methoxy, trifluoromethyl, $C_1$–$C_4$-alkylthio, $C_1$–$C_4$-alkylsulphinyl or $C_1$–$C_4$-alkylsulphonyl, $R_6$ is $C_1$–$C_6$-alkyl, cyclopropyl or cyclohexyl, and $R_7$ is methyl, ethyl, allyl, propargyl or 3-chloro-prop-2-en-1-yl.

4. Compounds of formula I according to claim 1, in which

R is hydrogen or $C_1$–$C_3$-alkyl,

A is $R_2$, $OR_3$ or $NR_3R_4$, $R_2$ is methoxymethyl or $C_1$–$C_4$-alkyl, $R_3$ is $C_1$–$C_4$-alkyl or is phenyl that is unsubstituted or is substituted by chlorine or by methyl, $R_4$ is hydrogen or methyl, B is one of the radicals

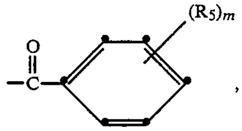 , 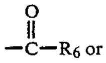 or 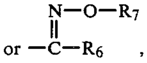 , m is 0, 1, 2 or 3, $R_5$ is chlorine, nitro, trifluoromethyl, methylthio, methylsulphinyl or methylsulphonyl, $R_6$ is $C_1$–$C_3$-alkyl or cyclopropyl, and $R_7$ is methyl, allyl, ethyl or 3-chloro-prop-2-en-1-yl.

5. Compounds of formula I according to claim 1, in which B is

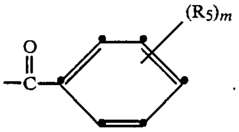 .

6. Compounds of formula I according to claim 1, in which B is

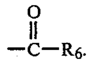 .

7. Compounds of formula I according to claim 1, in which B is

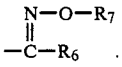 .

8. Compounds of formula I according to claim 1, in which A is $NR_3R_4$.

9. Compounds of formula I according to claim 1, in which A is $OR_3$.

10. Compounds of formula I according to claim 1, in which A is $R_2$.

11. 2-Butanoyl-5-ethoxycarbonylaminocyclohexan-1,3-dione, 2-Propanoyl-5-(N',N'-dimethylureido)-cyclohexan-1,3-dione, 2-Butanoyl-5-(N',N'-dimethylureido)-cyclohexan-1,3-dione, 5-Acetamido-2-propanoyl-cyclohexan-1,3-dione, 2-(2,4-Dichlorbenzoyl)-5-ethoxycarbonylamino-cyclohexan-1,3-dione, 2-(2,4-Dichlorbenzoyl)-5-(N'-isopropylureido)-cyclohexan-1,3-dione, 2-(2,4-Dichlorbenzoyl)-5-(N',N'-dimethylureido)-cyclohexan-1,3-dione, 5-(N'-tert-Butylureido)-2-(1-allyloxyiminobutyl)-cyclohexan-1,3-dione, 5-(N',N'-Dimethylureido)-2-(1-ethoxyiminopropyl)-cyclohexan-1,3-dione, 5-(N'-Phenylureido)-2-(1-ethoxyiminobutyl)-cyclohexan-1,3-dione, 5-(N'-Phenylureido)-2-[1-(3-chlorallyl)oxyiminobutyl]-cyclohexan-1,3-dione, 5-(N'-Phenylureido)-2-(1-ethoxyiminoethyl)-cyclohexan-1,3-dione, 5-(N'-Phenylureido)-2-(1-methoxyiminobutyl)-cyclohexan-1,3-dione, 5[N'-(2-Methylphenyl)-ureido]-2-(1-ethoxyiminobutyl)-cyclohexan-1,3-dione or 5-[N'-(3-Chlorphenyl)-ureido]-2-(1-ethoxyiminobutyl)-cyclohexan-1,3-dione according to claim 1.

12. A herbicidal or growth-regulating composition which contains as active ingredient an effective amount of a compound of formula I according to claim 1, together with carriers and/or other adjuvants.

13. A method of controlling undesired plant growth, which comprises treating the plants to be controlled or the locus thereof with a herbicidally effective amount of a compound of formula I according to claim 1.

14. A method of influencing the growth of cultivated plants, which comprises treating the plant or the locus thereof with a compound of formula I according to claim 1 in an amount capable of regulating growth.

* * * * *